(12) United States Patent
Brown et al.

(10) Patent No.: US 9,402,779 B2
(45) Date of Patent: Aug. 2, 2016

(54) COMPRESSION GARMENT WITH PERSPIRATION RELIEF

(71) Applicant: Covidien LP, Mansfield, MA (US)

(72) Inventors: Jennie Brown, Providence, RI (US); Kimbolt Young, Newtonville, MA (US); Paul DiCarlo, Middleboro, MA (US); Robert Degon, Bellingham, MA (US); Jon T. McIntyre, Newton, MA (US); Ryan Heller, Taunton, MA (US); Eric Meade, Bourne, MA (US)

(73) Assignee: COVIDIEN LP, Mansfield, MA (US)

( * ) Notice: Subject to any disclaimer, the term of this patent is extended or adjusted under 35 U.S.C. 154(b) by 559 days.

(21) Appl. No.: 13/792,363

(22) Filed: Mar. 11, 2013

(65) Prior Publication Data

US 2014/0257154 A1    Sep. 11, 2014

(51) Int. Cl.
*A61H 9/00* (2006.01)
*A61F 13/08* (2006.01)

(52) U.S. Cl.
CPC ........... *A61H 9/0078* (2013.01); *A61F 13/08* (2013.01); *A61H 2201/164* (2013.01); *A61H 2201/165* (2013.01); *A61H 2201/1635* (2013.01); *A61H 2201/1697* (2013.01); *A61H 2209/00* (2013.01)

(58) Field of Classification Search
CPC ........... A61H 9/00; A61H 9/0078; A61H 2201/1635; A61H 2201/164; A61H 2201/165; A61H 2201/1697; A61H 2209/00; A61F 13/08
USPC ..................... 601/148–151; 602/13
See application file for complete search history.

(56) References Cited

U.S. PATENT DOCUMENTS

| | | |
|---|---|---|
| 908,959 A | 1/1909 | Cooke |
| 2,489,388 A | 11/1949 | Rubin |
| 3,473,527 A | 10/1969 | Spiro |
| 3,504,675 A | 4/1970 | Bishop |
| 3,703,171 A | 11/1972 | Schiavitto |
| 3,824,492 A | 7/1974 | Brienza et al. |
| 3,831,467 A | 8/1974 | Moore |
| 3,868,952 A | 3/1975 | Hatton |
| 3,934,583 A | 1/1976 | Hollingshead et al. |
| 3,945,047 A | 3/1976 | Jarrell, Jr. |
| 4,021,860 A | 5/1977 | Swallow et al. |
| 4,091,804 A | 5/1978 | Hasty |
| 4,091,864 A | 5/1978 | Cocuzza et al. |
| 4,116,236 A | 9/1978 | Albert |
| 4,135,500 A | 1/1979 | Gorran |
| 4,201,203 A | 5/1980 | Applegate |
| 4,207,876 A | 6/1980 | Annis |

(Continued)

FOREIGN PATENT DOCUMENTS

| | | |
|---|---|---|
| AU | 2008234965 A1 | 5/2009 |
| DE | 1955539 A1 | 5/1971 |

(Continued)

OTHER PUBLICATIONS

Search Report dated Jul. 22, 2014 in related European Patent Application serial No. 14151774.8, 9 pages.

(Continued)

*Primary Examiner* — Quang D Thanh

(57) ABSTRACT

A compression garment includes a bladder having an inner surface and an outer surface. Wicking material may be present to wick fluid. In another version a removable absorbent material is releasably secured to the bladder.

9 Claims, 20 Drawing Sheets

FIG. 5

(56) References Cited

U.S. PATENT DOCUMENTS

| | | |
|---|---|---|
| 4,219,892 A | 9/1980 | Rigdon |
| D259,058 S | 4/1981 | Marshall |
| 4,320,746 A | 3/1982 | Arkans et al. |
| 4,340,064 A | 7/1982 | Vale |
| 4,353,362 A | 10/1982 | DeMarco |
| 4,363,125 A | 12/1982 | Brewer et al. |
| 4,375,217 A | 3/1983 | Arkans |
| 4,402,312 A | 9/1983 | Villari et al. |
| 4,425,912 A | 1/1984 | Harper |
| 4,442,834 A | 4/1984 | Tucker et al. |
| 4,445,505 A | 5/1984 | Labour et al. |
| 4,467,484 A | 8/1984 | Nagatake et al. |
| 4,492,227 A | 1/1985 | Senn et al. |
| 4,547,919 A | 10/1985 | Wang |
| 4,628,945 A | 12/1986 | Johnson, Jr. |
| 4,638,794 A | 1/1987 | Grisar |
| 4,700,698 A | 10/1987 | Kleylein |
| 4,702,234 A | 10/1987 | Huntjens |
| 4,724,831 A | 2/1988 | Huntjens |
| 4,765,318 A | 8/1988 | Tranberg et al. |
| 4,811,727 A | 3/1989 | Etienne |
| 4,872,448 A | 10/1989 | Johnson, Jr. |
| 4,938,207 A | 7/1990 | Vargo |
| 4,977,891 A | 12/1990 | Grim |
| 4,986,263 A | 1/1991 | Dickerson et al. |
| 4,989,273 A | 2/1991 | Cromartie |
| 5,107,823 A | 4/1992 | Fratesi |
| 5,125,400 A | 6/1992 | Johnson, Jr. |
| 5,134,726 A | 8/1992 | Ross |
| 5,144,708 A | 9/1992 | Pekar |
| 5,154,690 A | 10/1992 | Shiono |
| 5,185,000 A | 2/1993 | Brandt et al. |
| 5,230,335 A | 7/1993 | Johnson, Jr. et al. |
| 5,230,695 A | 7/1993 | Silver et al. |
| 5,261,871 A | 11/1993 | Greenfield |
| 5,263,923 A | 11/1993 | Fujimoto |
| 5,306,229 A | 4/1994 | Brandt et al. |
| 5,314,455 A | 5/1994 | Johnson, Jr. et al. |
| 5,334,135 A | 8/1994 | Grim et al. |
| 5,339,020 A | 8/1994 | Siligoni et al. |
| 5,353,525 A | 10/1994 | Grim |
| 5,378,224 A | 1/1995 | Billotti |
| 5,385,538 A | 1/1995 | Mann |
| 5,399,153 A | 3/1995 | Caprio, Jr. et al. |
| 5,407,421 A | 4/1995 | Goldsmith |
| 5,411,037 A | 5/1995 | Hess et al. |
| 5,417,720 A | 5/1995 | Mason |
| 5,419,161 A | 5/1995 | Bodenschatz et al. |
| 5,449,341 A | 9/1995 | Harris |
| 5,450,858 A | 9/1995 | Zablotsky et al. |
| 5,451,201 A | 9/1995 | Prengler |
| 5,462,517 A | 10/1995 | Mann |
| 5,466,250 A | 11/1995 | Johnson, Jr. et al. |
| 5,474,524 A | 12/1995 | Carey |
| 5,489,259 A | 2/1996 | Jacobs et al. |
| 5,496,262 A | 3/1996 | Johnson, Jr. et al. |
| 5,514,081 A | 5/1996 | Mann |
| 5,527,267 A | 6/1996 | Billotti |
| 5,554,105 A | 9/1996 | Taylor |
| 5,556,374 A | 9/1996 | Grace et al. |
| 5,582,584 A | 12/1996 | Billotti |
| 5,584,802 A | 12/1996 | Hess et al. |
| 5,588,955 A | 12/1996 | Johnson, Jr. et al. |
| 5,588,956 A | 12/1996 | Billotti |
| 5,613,943 A | 3/1997 | Palumbo |
| 5,626,556 A | 5/1997 | Tobler et al. |
| 5,626,557 A | 5/1997 | Mann |
| 5,630,792 A | 5/1997 | Neal |
| 5,640,714 A | 6/1997 | Tanaka |
| 5,641,322 A | 6/1997 | Silver et al. |
| 5,657,767 A | 8/1997 | Nelson et al. |
| 5,683,439 A | 11/1997 | Jensen |
| 5,690,672 A | 11/1997 | Cohen |
| 5,693,453 A | 12/1997 | Muroya |
| 5,695,452 A | 12/1997 | Grim et al. |
| 5,717,996 A | 2/1998 | Feldmann |
| 5,720,715 A | 2/1998 | Eriksson |
| 5,728,055 A | 3/1998 | Sebastian |
| 5,730,710 A | 3/1998 | Eichhorn et al. |
| 5,733,249 A | 3/1998 | Katzin et al. |
| 5,759,167 A | 6/1998 | Shields et al. |
| 5,785,669 A | 7/1998 | Proctor et al. |
| 5,785,673 A | 7/1998 | Billotti |
| 5,792,084 A | 8/1998 | Wilson et al. |
| 5,795,312 A | 8/1998 | Dye |
| 5,797,851 A | 8/1998 | Byrd |
| 5,823,981 A | 10/1998 | Grim et al. |
| 5,833,639 A | 11/1998 | Nunes et al. |
| 5,853,381 A | 12/1998 | Stevenson et al. |
| 5,876,359 A | 3/1999 | Bock et al. |
| 5,888,185 A | 3/1999 | Regan |
| 5,891,071 A | 4/1999 | Stearns et al. |
| 5,899,207 A | 5/1999 | Scheinberg |
| 5,925,010 A | 7/1999 | Caprio, Jr. |
| 6,006,751 A | 12/1999 | Spitzer |
| 6,024,714 A | 2/2000 | Katzin |
| 6,076,193 A | 6/2000 | Hood |
| 6,099,489 A | 8/2000 | Herzberg et al. |
| 6,126,683 A | 10/2000 | Momtaheni |
| 6,129,694 A | 10/2000 | Bodenschatz |
| 6,149,616 A | 11/2000 | Szlema et al. |
| 6,203,510 B1 | 3/2001 | Takeuchi et al. |
| 6,228,044 B1 | 5/2001 | Jensen et al. |
| 6,254,554 B1 | 7/2001 | Turtzo |
| 6,261,253 B1 | 7/2001 | Katzin |
| 6,279,160 B1 | 8/2001 | Chen |
| 6,287,269 B1 | 9/2001 | Osti et al. |
| 6,290,664 B1 | 9/2001 | Nauert |
| 6,306,112 B2 | 10/2001 | Bird |
| 6,308,353 B1 | 10/2001 | Van Steenburg |
| 6,338,722 B1 | 1/2002 | Barbe-Vicuna et al. |
| 6,385,778 B1 | 5/2002 | Johnson |
| 6,394,971 B1 | 5/2002 | Slautterback et al. |
| 6,425,195 B1 | 7/2002 | Donzis |
| 6,425,876 B1 | 7/2002 | Frangi et al. |
| 6,467,106 B1 | 10/2002 | Heimbrock |
| 6,520,926 B2 | 2/2003 | Hall |
| 6,526,597 B1 | 3/2003 | Shepard |
| 6,530,941 B1 | 3/2003 | Muller et al. |
| 6,551,280 B1 | 4/2003 | Knighton et al. |
| 6,553,572 B2 | 4/2003 | Fiorini et al. |
| 6,592,534 B1 | 7/2003 | Rutt et al. |
| 6,618,859 B1 | 9/2003 | Kadymir et al. |
| 6,682,547 B2 | 1/2004 | McEwen et al. |
| 6,689,079 B2 | 2/2004 | Flick et al. |
| 6,712,780 B2 | 3/2004 | Darcey |
| 6,849,057 B2 | 2/2005 | Satou et al. |
| 6,859,965 B1 | 3/2005 | Gourd |
| 6,923,777 B2 | 8/2005 | Garon |
| 6,945,944 B2 | 9/2005 | Kuiper et al. |
| 6,984,846 B2 | 1/2006 | Newns et al. |
| 6,994,682 B2 | 2/2006 | Bauerfeind et al. |
| 7,011,640 B2 | 3/2006 | Patterson et al. |
| 7,014,621 B2 | 3/2006 | Nelson |
| 7,028,690 B2 | 4/2006 | Schneider et al. |
| 7,044,924 B1 | 5/2006 | Roth et al. |
| 7,083,586 B2 | 8/2006 | Simmons et al. |
| 7,114,188 B1 | 10/2006 | Teigen |
| 7,173,161 B1 | 2/2007 | Kandt |
| 7,229,390 B2 | 6/2007 | Fujii et al. |
| 7,237,272 B2 | 7/2007 | Botcher |
| 7,238,080 B2 | 7/2007 | Gimble |
| 7,273,464 B2 | 9/2007 | Reinhardt |
| 7,282,038 B2 | 10/2007 | Gillis et al. |
| 7,306,568 B2 | 12/2007 | Diana |
| 7,326,227 B2 | 2/2008 | Dedo et al. |
| 7,442,175 B2 | 10/2008 | Meyer et al. |
| 7,465,283 B2 | 12/2008 | Grim et al. |
| 7,479,577 B2 | 1/2009 | Scheinberg et al. |
| 7,517,331 B2 | 4/2009 | Reinhardt et al. |
| 7,524,296 B2 | 4/2009 | Patterson et al. |
| 7,559,908 B2 | 7/2009 | Ravikumar |
| 7,562,541 B2 | 7/2009 | Hermanson et al. |
| 7,591,797 B2 | 9/2009 | Hakonson et al. |

(56) References Cited

U.S. PATENT DOCUMENTS

| | | |
|---|---|---|
| 7,615,027 B2 | 11/2009 | Nordt, III et al. |
| 7,658,720 B2 | 2/2010 | Johnson, III |
| 7,670,306 B2 | 3/2010 | Nordt, III et al. |
| 7,690,380 B2 | 4/2010 | Lee et al. |
| 7,708,707 B2 | 5/2010 | Cook et al. |
| 7,741,966 B2 | 6/2010 | Bonnefin et al. |
| 7,749,182 B2 | 7/2010 | Gramza et al. |
| 7,780,698 B2 | 8/2010 | McEwen et al. |
| 7,842,000 B2 | 11/2010 | Lai et al. |
| 7,862,527 B2 | 1/2011 | Gramza et al. |
| 7,871,387 B2 | 1/2011 | Tordella et al. |
| 7,909,786 B2 | 3/2011 | Bonnefin et al. |
| 7,931,606 B2 | 4/2011 | Meyer |
| 7,937,771 B2 | 5/2011 | Mazzarolo |
| 7,942,840 B2 | 5/2011 | Hargrave et al. |
| 7,945,970 B2 | 5/2011 | Belluye et al. |
| 7,947,003 B2 | 5/2011 | Bonnefin et al. |
| 8,007,457 B2 | 8/2011 | Taylor |
| 8,016,778 B2 | 9/2011 | Brown et al. |
| 8,016,779 B2 | 9/2011 | Brown et al. |
| 8,021,388 B2 | 9/2011 | Brown et al. |
| 8,029,450 B2 | 10/2011 | Brown et al. |
| 8,029,451 B2 | 10/2011 | Beyer et al. |
| 8,034,007 B2 | 10/2011 | Avitable et al. |
| 8,065,753 B2 | 11/2011 | Sorensen et al. |
| 8,070,699 B2 | 12/2011 | Avitable et al. |
| 8,075,507 B2 | 12/2011 | Linnane et al. |
| 8,109,892 B2 | 2/2012 | Brown et al. |
| 8,114,117 B2 | 2/2012 | Avitable |
| 8,118,762 B2 | 2/2012 | Bort |
| 8,118,765 B2 | 2/2012 | Magnusson |
| 8,128,583 B2 | 3/2012 | Ghatge |
| 8,137,378 B2 | 3/2012 | McEwen et al. |
| 8,142,472 B2 | 3/2012 | McEwen et al. |
| 8,162,861 B2 | 4/2012 | Avitable et al. |
| 8,192,380 B2 | 6/2012 | Nardi |
| 8,216,169 B2 | 7/2012 | Koby et al. |
| 8,226,585 B2 | 7/2012 | Pick et al. |
| 8,235,923 B2 | 8/2012 | Avitable et al. |
| 8,262,594 B2 | 9/2012 | Sandusky et al. |
| 8,313,450 B2 | 11/2012 | Ben-Nun |
| 8,314,283 B2 | 11/2012 | Kingsford et al. |
| 8,317,736 B2 | 11/2012 | Virjus et al. |
| 8,347,415 B2 | 1/2013 | Mazzarolo |
| 8,419,666 B2 | 4/2013 | Liu et al. |
| 8,469,910 B2 | 6/2013 | Ganapathy et al. |
| 8,505,120 B2 | 8/2013 | Lambertz |
| 8,506,508 B2 | 8/2013 | Avitable et al. |
| 2002/0068886 A1 | 6/2002 | Lin |
| 2002/0147422 A1 | 10/2002 | Darcey et al. |
| 2003/0028157 A1 | 2/2003 | Jusiak et al. |
| 2003/0171706 A1 | 9/2003 | Nelson |
| 2004/0097855 A1 | 5/2004 | Page et al. |
| 2004/0167456 A1 | 8/2004 | Kingsford et al. |
| 2004/0176715 A1 | 9/2004 | Nelson |
| 2005/0070828 A1 | 3/2005 | Hampson et al. |
| 2005/0131489 A1 | 6/2005 | Gardon-Mollard |
| 2005/0165340 A1 | 7/2005 | Dunn |
| 2005/0283106 A1 | 12/2005 | Smith et al. |
| 2006/0010574 A1 | 1/2006 | Linnane et al. |
| 2006/0026736 A1 | 2/2006 | Nordt et al. |
| 2006/0135894 A1 | 6/2006 | Linnane et al. |
| 2006/0229541 A1 | 10/2006 | Hassler et al. |
| 2006/0287672 A1 | 12/2006 | McEwen et al. |
| 2007/0038167 A1 | 2/2007 | Tabron et al. |
| 2007/0049852 A1 | 3/2007 | Linnane et al. |
| 2007/0060857 A1 | 3/2007 | Testa, Jr. |
| 2007/0135836 A1 | 6/2007 | McEwen et al. |
| 2007/0179210 A1 | 8/2007 | Swaniker |
| 2007/0249976 A1 | 10/2007 | Tucker et al. |
| 2008/0103422 A1 | 5/2008 | Perry et al. |
| 2008/0189829 A1 | 8/2008 | Fusco |
| 2008/0245361 A1 | 10/2008 | Brown |
| 2008/0249441 A1* | 10/2008 | Avitable ............... A61H 9/0078 601/151 |
| 2008/0249443 A1* | 10/2008 | Avitable ............... A61H 9/0078 601/152 |
| 2008/0249559 A1 | 10/2008 | Brown et al. |
| 2008/0250551 A1 | 10/2008 | Mazzarolo |
| 2008/0306420 A1 | 12/2008 | Vess |
| 2009/0005717 A1 | 1/2009 | Brzank |
| 2009/0013450 A1 | 1/2009 | Lambertz |
| 2009/0126081 A1 | 5/2009 | Lambertz |
| 2009/0171384 A1 | 7/2009 | Hack |
| 2009/0227918 A1 | 9/2009 | Nardi et al. |
| 2009/0260639 A1 | 10/2009 | Hsu et al. |
| 2009/0312681 A1 | 12/2009 | NcSpadden et al. |
| 2010/0004575 A1 | 1/2010 | Vess |
| 2010/0016771 A1 | 1/2010 | Arbesman et al. |
| 2010/0036303 A1 | 2/2010 | Bauerfeind et al. |
| 2010/0037369 A1 | 2/2010 | Reichert |
| 2010/0056966 A1 | 3/2010 | Toth |
| 2011/0077565 A1 | 3/2011 | Hanlon et al. |
| 2012/0065664 A1 | 3/2012 | Avitable et al. |
| 2012/0071801 A1 | 3/2012 | Avitable |

FOREIGN PATENT DOCUMENTS

| | | |
|---|---|---|
| DE | 8115670 U1 | 8/1981 |
| DE | 8123588 U1 | 12/1981 |
| DE | 8503139 U1 | 5/1985 |
| DE | 8514142 U1 | 8/1985 |
| DE | 3416231 A1 | 11/1985 |
| DE | 3511250 A1 | 11/1985 |
| DE | 8529092 U1 | 1/1986 |
| DE | 3637879 A1 | 5/1988 |
| DE | 8800950 U1 | 5/1988 |
| DE | 8808422 U1 | 10/1988 |
| DE | 3838582 A1 | 1/1990 |
| DE | 8910985 U1 | 1/1990 |
| DE | 9004974 U1 | 9/1990 |
| DE | 9112765 U1 | 2/1992 |
| DE | 9115983 U1 | 4/1992 |
| DE | 9113898 U1 | 5/1992 |
| DE | 9300600 U1 | 4/1993 |
| DE | 9300615 U1 | 4/1993 |
| DE | 9304628 U1 | 9/1993 |
| DE | 4103383 C2 | 12/1993 |
| DE | 9316342 U1 | 2/1994 |
| DE | 9317021 U1 | 3/1994 |
| DE | 9408096 U1 | 9/1994 |
| DE | 9417219 U1 | 2/1995 |
| DE | 9417712 U1 | 2/1995 |
| DE | 29519978 U1 | 4/1996 |
| DE | 29519979 U1 | 4/1996 |
| DE | 29519980 U1 | 4/1996 |
| DE | 4091302 C2 | 5/1996 |
| DE | 29803103 U1 | 6/1998 |
| DE | 3802338 C2 | 7/1998 |
| DE | 20022041 U1 | 4/2001 |
| DE | 20020518 U1 | 5/2001 |
| DE | 20005661 U1 | 9/2001 |
| DE | 20005663 U1 | 9/2001 |
| DE | 29824758 U1 | 8/2002 |
| DE | 19849710 C2 | 10/2002 |
| DE | 20203275 U1 | 8/2003 |
| DE | 10305277 A1 | 9/2003 |
| DE | 202004004852 U1 | 7/2004 |
| DE | 102004019007 A1 | 11/2005 |
| DE | 202004013159 U1 | 2/2006 |
| DE | 202005020235 U1 | 4/2006 |
| DE | 102005012338 A1 | 9/2006 |
| DE | 202006009050 U1 | 10/2006 |
| DE | 202009008302 U1 | 9/2009 |
| EP | 0027172 A1 | 4/1981 |
| EP | 0070538 A1 | 1/1983 |
| EP | 0071818 A1 | 2/1983 |
| EP | 0010389 B1 | 6/1983 |
| EP | 0088832 A1 | 9/1983 |
| EP | 0115029 A1 | 8/1984 |
| EP | 0154758 A1 | 9/1985 |
| EP | 0159679 A2 | 10/1985 |
| EP | 0229577 A1 | 7/1987 |
| EP | 0262638 A2 | 4/1988 |

(56) References Cited

FOREIGN PATENT DOCUMENTS

| | | |
|---|---|---|
| EP | 0272989 A1 | 6/1988 |
| EP | 0277199 A1 | 8/1988 |
| EP | 0313487 A1 | 4/1989 |
| EP | 0329815 A1 | 8/1989 |
| EP | 0485943 A1 | 5/1992 |
| EP | 0492328 A1 | 7/1992 |
| EP | 0562967 A1 | 9/1993 |
| EP | 0598291 A1 | 5/1994 |
| EP | 0600218 A2 | 6/1994 |
| EP | 0602317 A2 | 6/1994 |
| EP | 0608223 A1 | 8/1994 |
| EP | 0628297 A1 | 12/1994 |
| EP | 0694296 A1 | 1/1996 |
| EP | 0746286 A1 | 12/1996 |
| EP | 0797933 A2 | 10/1997 |
| EP | 0835085 A1 | 4/1998 |
| EP | 0860153 A1 | 8/1998 |
| EP | 0898949 A1 | 3/1999 |
| EP | 0970670 A1 | 1/2000 |
| EP | 1050287 A1 | 11/2000 |
| EP | 1208822 A2 | 5/2002 |
| EP | 1289455 A1 | 3/2003 |
| EP | 1953284 A2 | 8/2008 |
| EP | 2090273 A2 | 8/2009 |
| FR | 2807644 A1 | 10/2001 |
| GB | 2061086 A | 5/1981 |
| GB | 2212399 A | 7/1989 |
| GB | 2260686 A | 4/1993 |
| GB | 2279255 A | 1/1995 |
| GB | 2300808 A | 11/1996 |
| GB | 2309168 A | 7/1997 |
| GB | 2373444 A | 9/2002 |
| GB | 2438365 A | 11/2007 |
| JP | 2009000277 A | 1/2009 |
| WO | 8502109 A1 | 5/1985 |
| WO | 8801855 A1 | 3/1988 |
| WO | 9101701 A1 | 2/1991 |
| WO | 9203110 A1 | 3/1992 |
| WO | 9207527 A1 | 5/1992 |
| WO | 9320789 A1 | 10/1993 |
| WO | 9417765 A1 | 8/1994 |
| WO | 9421201 A1 | 9/1994 |
| WO | 9833456 A1 | 8/1998 |
| WO | 0074619 A1 | 12/2000 |
| WO | 0103624 A1 | 1/2001 |
| WO | 0119299 A1 | 3/2001 |
| WO | 0121119 A1 | 3/2001 |
| WO | 0211827 A1 | 2/2002 |
| WO | 03041621 A1 | 5/2003 |
| WO | 2004041146 A1 | 5/2004 |
| WO | 2005007045 A1 | 1/2005 |
| WO | 2005060888 A1 | 7/2005 |
| WO | 2005120500 A2 | 12/2005 |
| WO | 2006083865 A2 | 8/2006 |
| WO | 2006091735 A2 | 8/2006 |
| WO | 2007018484 A1 | 2/2007 |
| WO | 2007067076 A1 | 6/2007 |
| WO | 2007111922 A2 | 10/2007 |
| WO | 2007147980 A2 | 12/2007 |
| WO | 2008126963 A1 | 10/2008 |
| WO | 2009015418 A1 | 2/2009 |
| WO | 2009025321 A1 | 2/2009 |
| WO | 2009093180 A1 | 7/2009 |

OTHER PUBLICATIONS

Office Action dated Aug. 5, 2014 in related Australian Patent Application serial No. 2014200495, 4 pages.
Office Action dated Sep. 6, 2015 in related Chinese Application No. 201410081591.X, 13 pages.
Office Action dated Jun. 2, 2015 in related Korean patent application serial No. 10-2015-39900, 8 pages.
Office Action dated Jan. 23, 2015 in related Korean application 10-201426557, 6 pages.

* cited by examiner

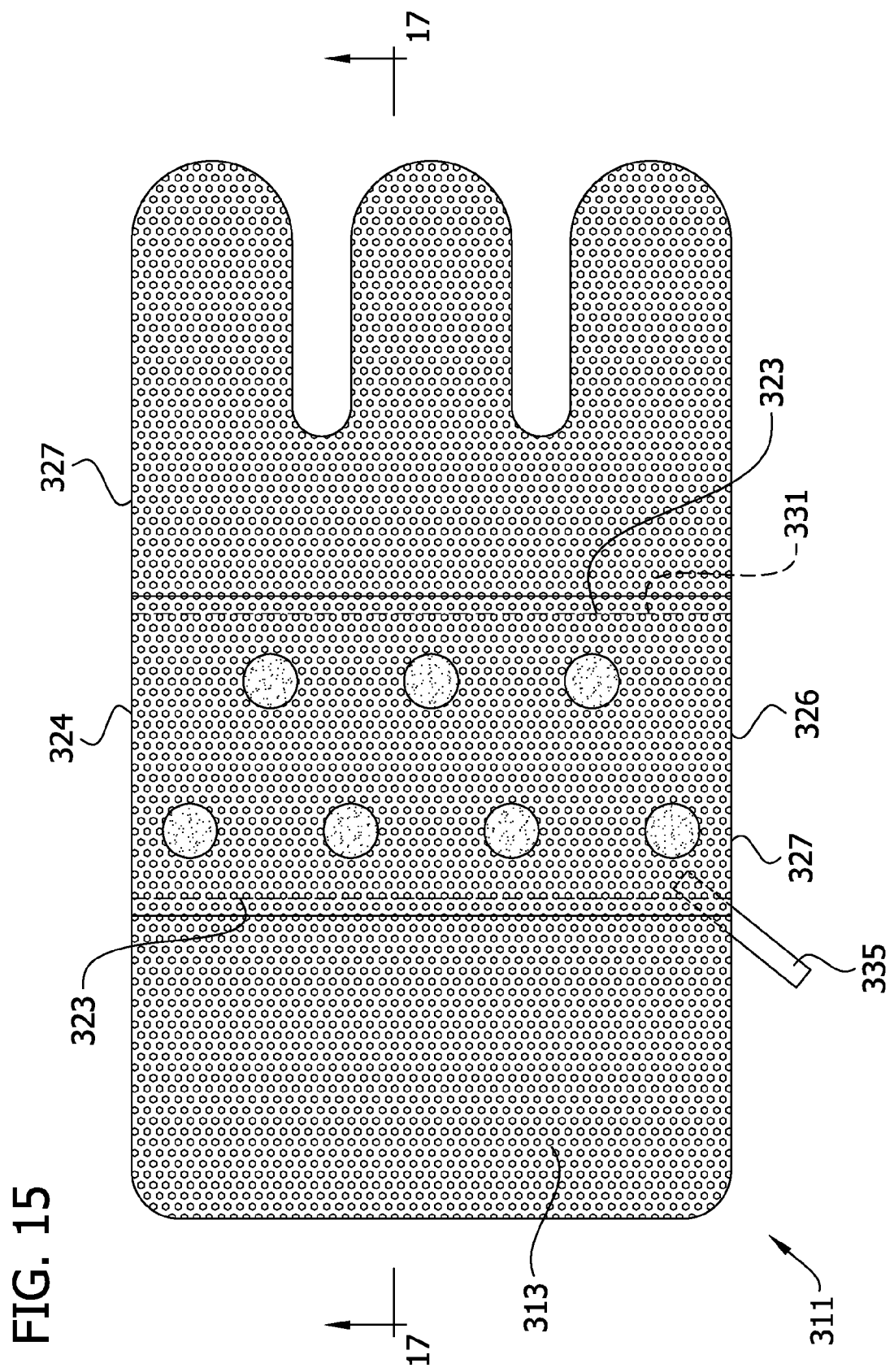

COMPRESSION GARMENT WITH PERSPIRATION RELIEF

TECHNICAL FIELD

The present disclosure generally relates to compression garments, and more particularly to a compression garments providing perspiration relief.

BACKGROUND OF THE INVENTION

A major concern for immobile patients and like persons are medical conditions that form clots in the blood, such as, deep vein thrombosis (DVT) and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal and tibial return deoxygenated blood to the heart. For example, when blood circulation in these veins is retarded due to illness, injury or inactivity, there is a tendency for blood to accumulate or pool. A static pool of blood may lead to the formation of a blood clot. A major risk associated with this condition is interference with cardiovascular circulation. Most seriously, a fragment of the blood clot can break loose and migrate. A pulmonary embolus can form from the fragment and can potentially block a main pulmonary artery, which may be life threatening.

The conditions and resulting risks associated with patient immobility may be controlled or alleviated by applying intermittent pressure with to a patient's limb, such as, for example, a leg to assist in blood circulation. This can be done with a compression sleeve. The impermeability of the sleeve makes it uncomfortable for the patient because moisture (i.e. perspiration) is trapped between the sleeve and the patient's body part. Retained moisture is irritating to the skin and unsanitary. This leads to the patient's unwillingness to wear the sleeve, thereby potentially endangering the health of the patient. Moreover, the sleeve is generally non-stretchable and bulky, restricting the mobility of the patient. Also chafing of a patient's limb can occur as a result of the sleeve. The final construction of a prior art sleeve is bulky, rigid and may feel heavy to a person over an extended period of use.

SUMMARY OF THE INVENTION

In a first aspect, a compression garment generally comprises an inflatable bladder having an inner surface, an outer surface substantially opposite the inner surface, and opposing side edges extending longitudinally along a length of the bladder. At least a portion of the bladder defines a compression region expandable to apply pressure to a portion of a wearer's body. A non-wicking material welded to the opposing side edges of the bladder so that the non-wicking material extends laterally away from the side edges of the bladder has an inner surface and an outer surface substantially opposite the inner surface. A wicking material is disposed on the inner surface of the non-wicking material for wicking fluid away from the portion of the wearer's body.

In said first aspect, where the wicking material extends partially over the inner surface of the bladder.

In said first aspect, where the bladder further comprises a center portion and side portions, the center portion is disposed between the side portions. The wicking material extends over the side portions, and the center portion is uncovered by the wicking material.

In said first aspect, where the wicking material comprises two layers, each layer separate and spaced apart from the other layer.

In said first aspect, where the wicking material extends over the entire inner surface of the non-wicking material.

In said first aspect, where the wicking material extending over the side portions of the bladder is welded to the bladder within the compression region, and the wicking material extending over the non-wicking material is welded around a perimeter of the non-wicking material.

In said first aspect, where the wicking material extends over the entire inner surface of the bladder.

In said first aspect, where the non-wicking material comprises foam.

In said first aspect, where the compression garment further comprises a breathable outer cover disposed over the outer surface of the bladder.

In a second aspect, a compression garment generally comprises an inflatable bladder having an inner surface, an outer surface, and opposing side edges extending longitudinally along a length of the bladder. At least a portion of the bladder defines a compression region expandable to apply pressure to a part of a wearer's body. Wicking material is attached to the bladder and extends over at least a portion and less than the entirety of the inner surface of the bladder for wicking fluid away from the bladder.

In said second aspect, where the bladder further comprises a center portion and side portions. The center portion is disposed between the side portions. Wicking material extends over the side portions, and the center portion is uncovered by the wicking material.

In said second aspect, where the wicking material extending over the side portions of the bladder is welded to the bladder within the compression region.

In said second aspect, where the wicking material comprises two layers, each layer separate and spaced apart from the other layer.

In said second aspect, where the compression garment further comprises an absorbent, non-wicking material disposed over the inner surface of the bladder for holding fluid at the part of the wearer's body, wherein the wicking material contacts the absorbent material to draw the fluid away from the part of the wearer's body.

In said second aspect, where at least a portion of the wicking material is disposed between the bladder and the absorbent material.

In said second aspect, where the absorbent material comprises a polyethylene SMS (spunbound-meltblown-spunbound) material.

In said second aspect, where the absorbent material is releasably attached to the bladder and wicking material.

In said second aspect, the compression garment further comprises a breathable outer cover disposed over the outer surface of the bladder.

In a third aspect, a compression garment generally comprises a bladder having an inner surface and an outer surface. A first wicking layer is disposed on the inner surface of the bladder, and a second wicking layer is disposed on the outer surface of the bladder. An inner layer is disposed on an inner surface of the first wicking layer.

In said third aspect, where the bladder further has a top edge, a bottom edge, and opposing side edges, and the first and second wicking layers extend laterally beyond the opposing side edges of the bladder.

In said third aspect, where the first and second wicking layers engage each other beyond the opposing side edges of the bladder to transfer moisture between the first and second wicking layers.

In said third aspect, where the compression garment further comprises an outer layer disposed on an outer surface of second wicking layer and defining an outermost surface of the garment.

In said third aspect, where the inner layer has openings in registration with the first wicking layer.

In said third aspect, where the outer layer has openings in registration with the second wicking layer.

In said third aspect, where each of the openings in each of the inner and outer layers has an area of about 0.61 in$^2$.

In said third aspect, where the bladder further includes top and bottom edges, and the bladder is attached to the inner and outer layers only at the top and bottom edges of the bladder.

In said third aspect, where the inner and outer layers are welded to the bladder at the top and bottom edges of the bladder.

In said third aspect, where the inner and outer layers are stitched to the bladder at the top and bottom edges of the bladder.

In a fourth aspect, a compression garment generally comprises an inner layer and an outer layer in generally opposing relation with each other, the inner and outer layers being sized to wrap around the part of the wearer's body. A bladder having an inner face, an outer face, a top edge and a bottom edge is disposed between the inner and outer layers. The bladder is attached to the inner and outer layers only at the top and bottom edges of the bladder. Wicking material extends to the top and bottom edges of the bladder and is configured for transferring fluid around the bladder from the inner face to the outer face of the bladder.

In said fourth aspect, where the inner and outer layers are welded to the bladder at the top and bottom edges of the bladder.

In said fourth aspect, where the inner and outer layers are stitched to the bladder at the top and bottom edges of the bladder.

In said fourth aspect, where the bladder includes two opposing side edges and the wicking material extends laterally beyond the side edges of the bladder.

In said fourth aspect, where the inner layer has openings in registration with the wicking material.

In said fourth aspect, where each of the openings in the inner layer have an area of about 0.61 in$^2$.

In said fourth aspect, where the bladder further comprises two sheets of flexible material sealed together.

In said fourth aspect, where the wicking material is disposed between the bladder and the inner layer and between the bladder and the outer layer.

In a fifth aspect, a compression garment generally comprises an inflatable bladder having an inner surface and an outer surface opposite the inner surface, at least a portion of the bladder defining a compression region expandable to apply pressure to a part of a wearer's body. An absorbent, non-wicking material is releasably securable to the bladder for holding fluid at the part of the wearer's body. The bladder and absorbent non-wicking material are mountable on the wearer's body part.

In said fifth aspect, where the absorbent material is releasably securable to the bladder on the inner surface thereof.

In said fifth aspect, where the compression garment further comprises an inner liner releasably attached to the garment and defining a pocket wherein the absorbent material is releasably secured to the bladder.

In said fifth aspect, where the inner liner is releasably attached to the inner surface of the bladder.

In said fifth aspect, where the inner liner comprises a wicking material in direct contact with an inner surface of the absorbent material to draw the fluid away from the part of the wearer's body for absorption by the absorbent material.

In said fifth aspect, where the inner liner is releasably attached to the bladder by hook and loop fasteners.

In said fifth aspect, where the absorbent material comprises a polyethylene SMS (spunbound-meltblown-spunbound) material.

In said fifth aspect, where the compression garment further comprises an outer garment layer attached to the outer surface of the bladder.

Other objects and features will be in part apparent and in part pointed out hereinafter.

BRIEF DESCRIPTION OF THE DRAWINGS

FIG. 15 is a rear view of a compression sleeve.

Corresponding reference characters indicate corresponding parts throughout the drawings.

DETAILED DESCRIPTION

Referring now to FIGS. 1-7, a compression garment (or "sleeve") 11 applies repeated compression therapy to a limb of a wearer. The sleeve 11 is a knee-length sleeve positionable around a leg of the wearer. It will be understood that the compression sleeve may come in different configurations, such as a thigh-length sleeve. Other types of compression devices for being disposed about other limbs of the wearer's body are also within the scope of this disclosure. These include, for example, devices that do not apply compression repeatedly and/or devices that apply sequential compression.

Figures 4, 5:
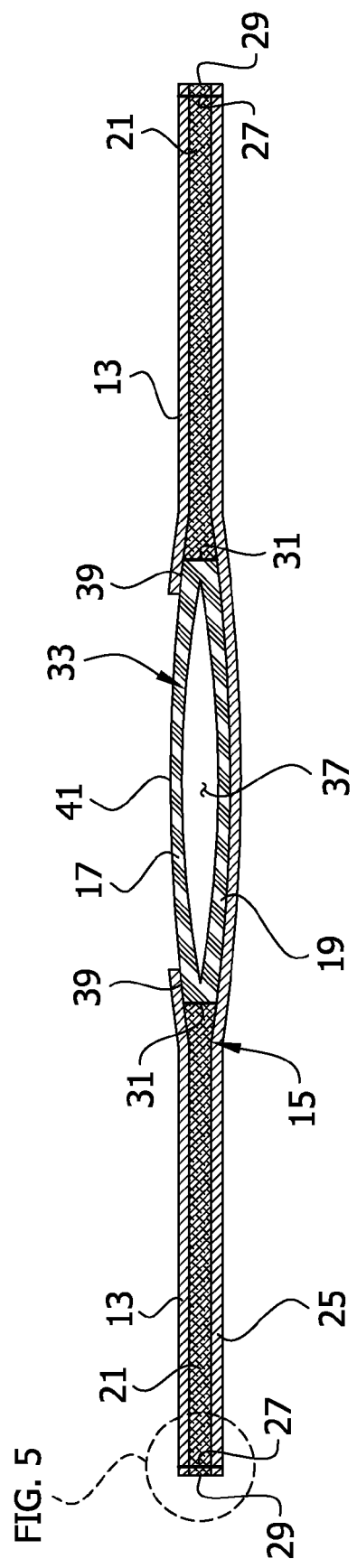
FIG. 4 is a section taken through line 4-4 in FIG. 2.
FIG. 5 is an enlarged detail of a seam line shown in FIG. 4.
Figure 5:
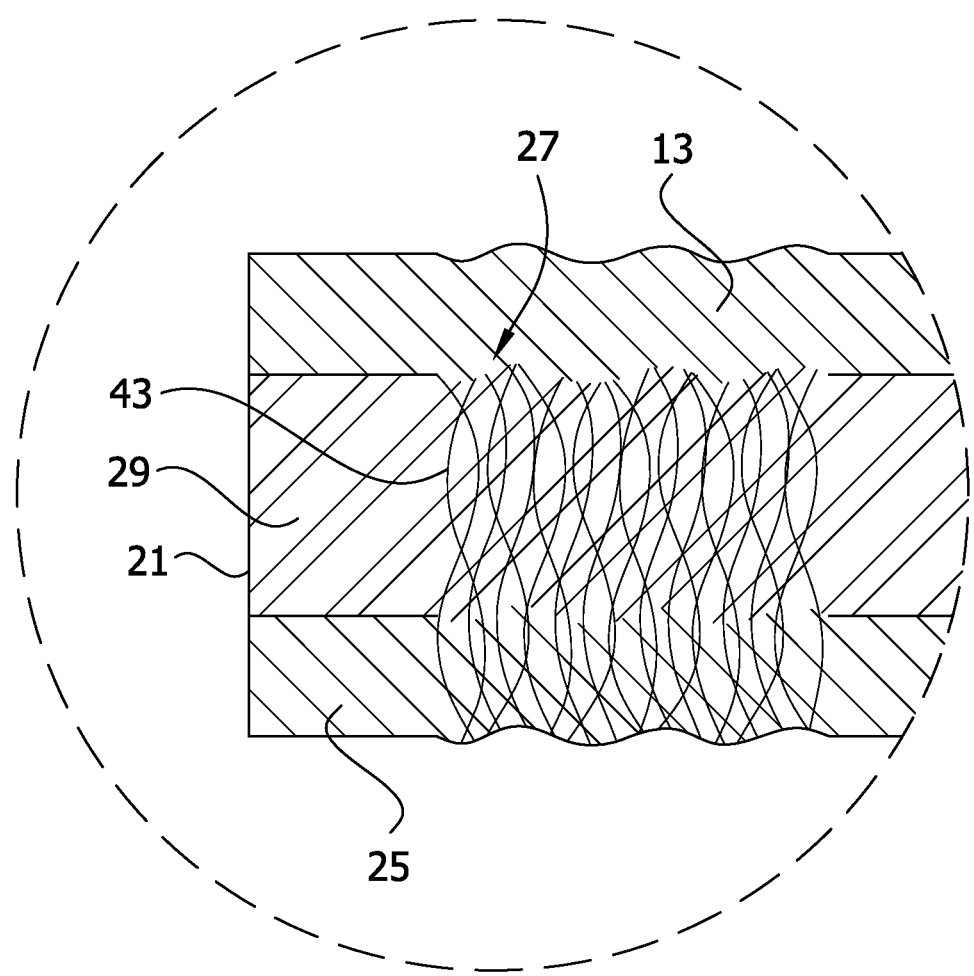
Figure 6:
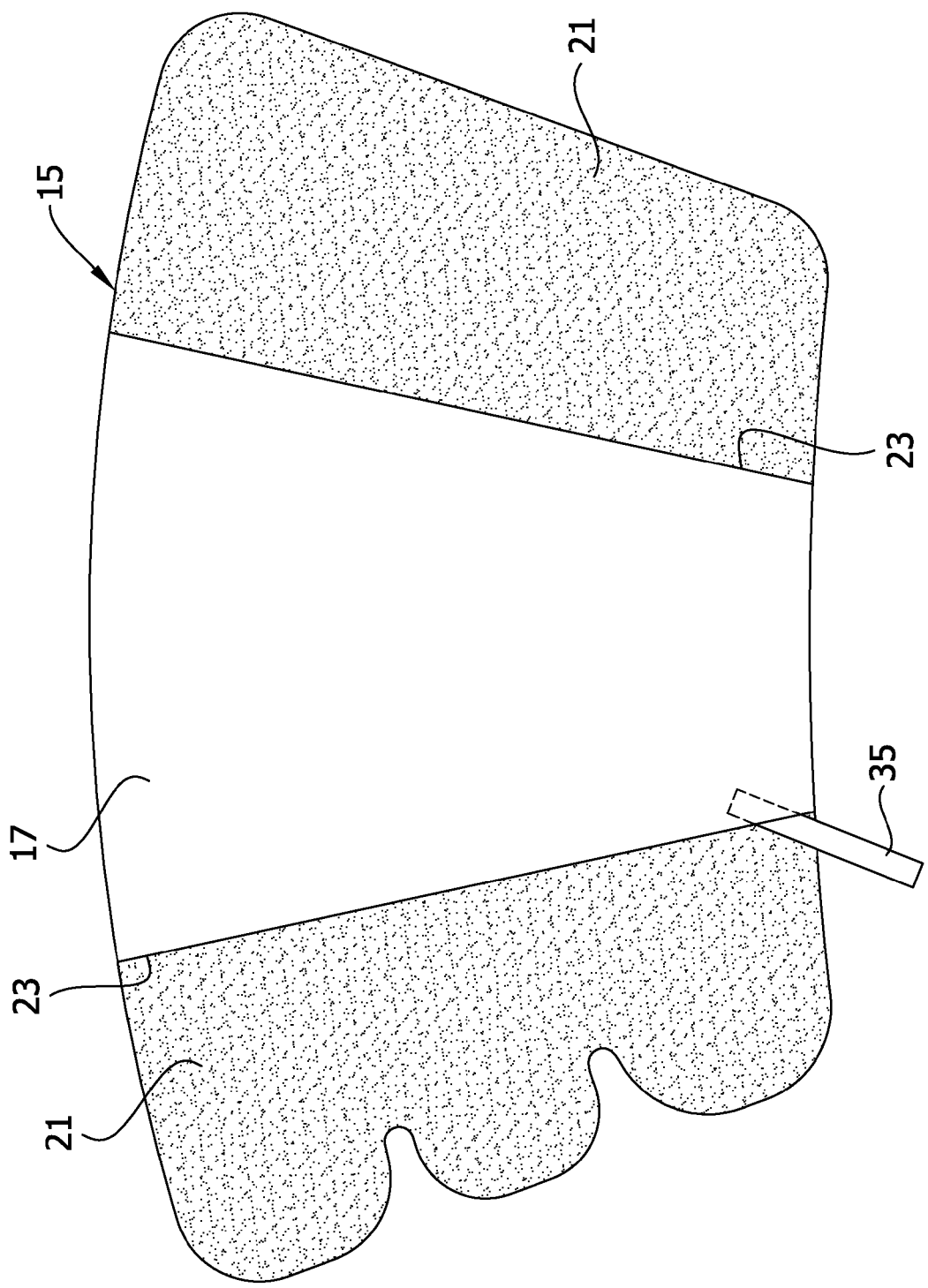
FIG. 6 is a rear view of the sleeve of FIG. 1 with wicking material of the sleeve removed.

The compression sleeve 11 includes a pair of inner layers 13, on which an intermediate layer composite 15 is overlaid (FIGS. 4 and 6). The layer composite 15 includes a first bladder layer 17 and a second bladder layer 19 overlaid on the first bladder layer and secured thereto. The intermediate layer composite 15 also includes a pair of intermediate garment layers 21 secured to opposing side edges 23 of the first and second bladder layers 17, 19 and extending transversely away from the bladder layers. An outer layer (or cover) 25 overlies and is secured to the second bladder layer 19 and intermediate garment layers 21 (FIG. 4). The layers of the sleeve 11 may be secured together by radiofrequency welding, adhesive, or other chemical and/or mechanical process. The layers are secured by a weld 27 about a periphery 29 of the sleeve 11. In use, the inner layers 13 and the first bladder layer 17 may be disposed for contacting the wearer's skin when the sleeve is worn, and the outer cover 25 may be most distant from the wearer's skin when the sleeve is worn. While a specific configuration of layers has been described above, it should be appreciated that other configurations of the sleeve 11 are also within the scope of this disclosure.

The first and second bladder layers 17, 19 respectively, may each include a single sheet of elastic material (broadly, "bladder material"). For example, the sheets 17, 19 can be made of a pliable PVC material. The inner layers 13 and the outer cover 25 can be made of a polyester material. The inner layers 13 can, additionally or alternatively, be formed from wicking material and can have a soft texture to provide a comfortable interface with the wearer's body. The first and second bladder layers 17, 19 are sealingly secured to each other along bladder seam lines 31 forming a bladder 33. The bladder 33 defines an interior space 37 such that the bladder 33 expands and contracts under the influence of air pressure or other fluids delivered through a conduit 35 in communication with the interior space 37 of the bladder 33. The interior space 37 defines a compression region of the bladder 33, the compression region being generally bounded by the seam lines 31, which provide an air or water tight boundary for the compression region. The bladder layers 17, 19 may be secured together at locations other than the seam lines 31, for example, to form multiple bladders. The seams 31 also attach the intermediate garment layers 21 to the bladder layers 17, 19. The intermediate layers 21 can be formed from a non-wicking material such as foam.

Figure 1:
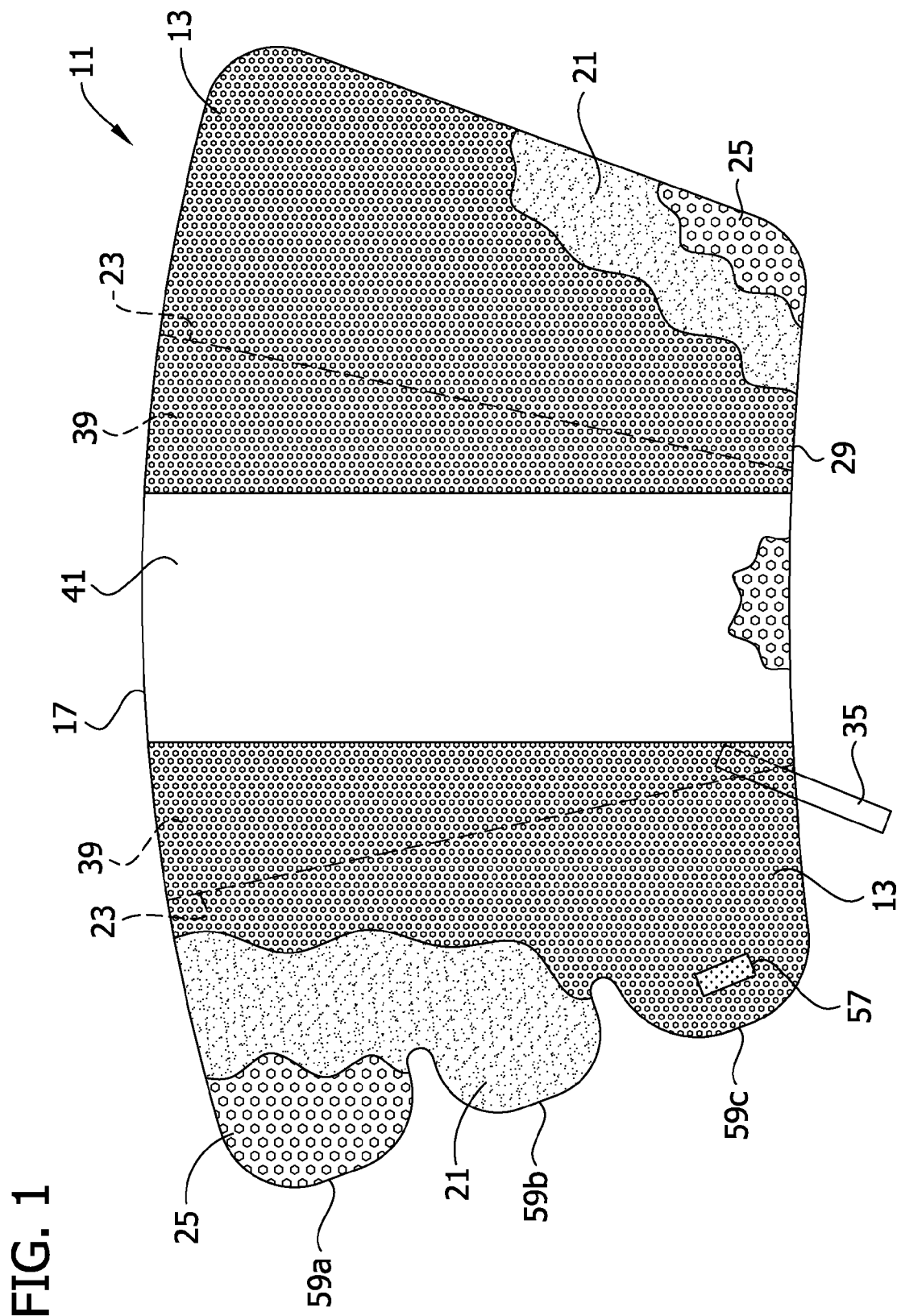
FIG. 1 is a rear view of a compression sleeve with portions of the sleeve broken away.
Figure 2:
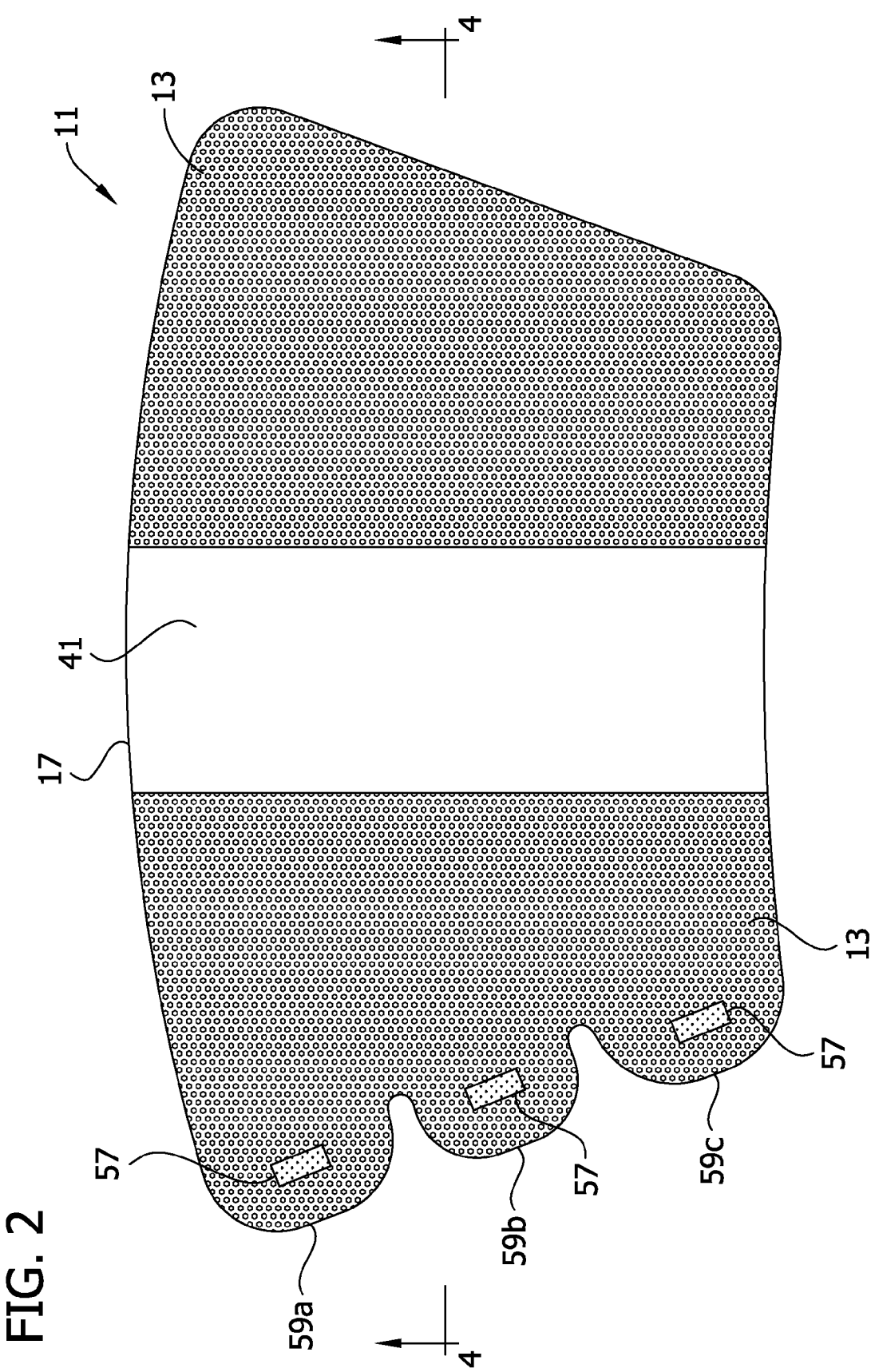
FIG. 2 is a rear view of the sleeve of FIG. 1.
Figure 3:
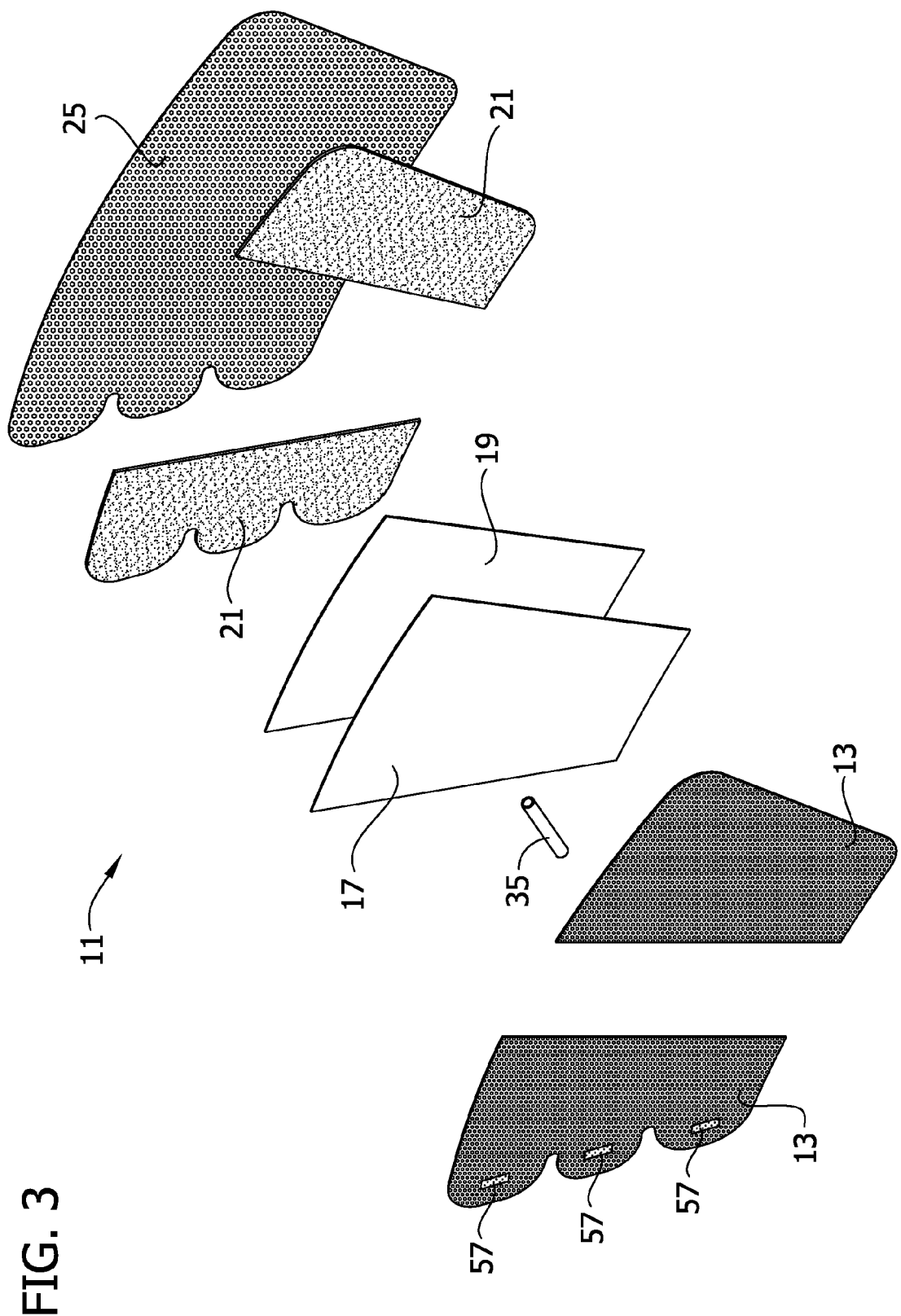
FIG. 3 is an exploded perspective of the sleeve of FIG. 1.

Referring to FIGS. 1 and 4, the inner layers 13 extend partially over the first bladder layer 17 to cover only a portion of the bladder 33. Therefore, the inner layers 13 cover side portions 39 of the bladder 33, leaving exposed a center portion 41 of the bladder 33. As will be explained in greater detail below, this will wick fluid from a location under the bladder 33 to a location outside a perimeter of the bladder. Once the fluid is transported away from the bladder 33, it can be more readily evaporated to the atmosphere. Therefore, this construction of the sleeve 11 reduces fluid build-up in and under the sleeve 11, for example, to help reduce the likelihood of saturation of the sleeve.

Referring to FIGS. 1, 2, 4, and 5, the inner layers 13 can be constructed of a material that is capable of wicking moisture away from a wearer's skin. The inner (or "wicking") layers 13, through capillary action along a yarn filament surface of the layers, draw in moisture trapped near the skin of the wearer, and carry the moisture away from the surface of the skin, transporting the moisture from locations on the skin near the inner layers, where moisture can be abundant, to areas where moisture is less abundant and more easily for evaporated to the ambient environment. Suitable wicking materials may include, for example, some forms of polyester, polypropylene, and/or other materials. Microfibers may be used. Suitable materials include, but are not limited to, 100% polyester tricot knit CoolDry mesh fabric 75D/72F, sold by HTT Corporation, Fujian Province, China and CoolMax®, sold by E. I. du Pont de Nemours and Company, Wilmington, Del.

The seam line 27 allows fluid wicked by the inner layers 13 to travel, through the intermediate layers 21, to the outer cover 25, where the fluid can evaporate into the atmosphere. The outer cover 25, intermediate layers 21 and the inner layers 13 may be secured to one another in a single welding step, such as by a radiofrequency welder, after the layers have been stacked on one another. During this step, the intermediate layers 21 are heated and softened along the seam line 27. The softening of the intermediate layers 21 is one way that fibers 43 of the inner layers 13 extend entirely through the seam line 27 to the exterior of the compression sleeve 11. The fibers 43 are distributed generally uniformly throughout inner layers 13. Thus, the inner layers 13 are able to wick fluid through the seam line 27 for evaporating into the atmosphere.

Figure 7:
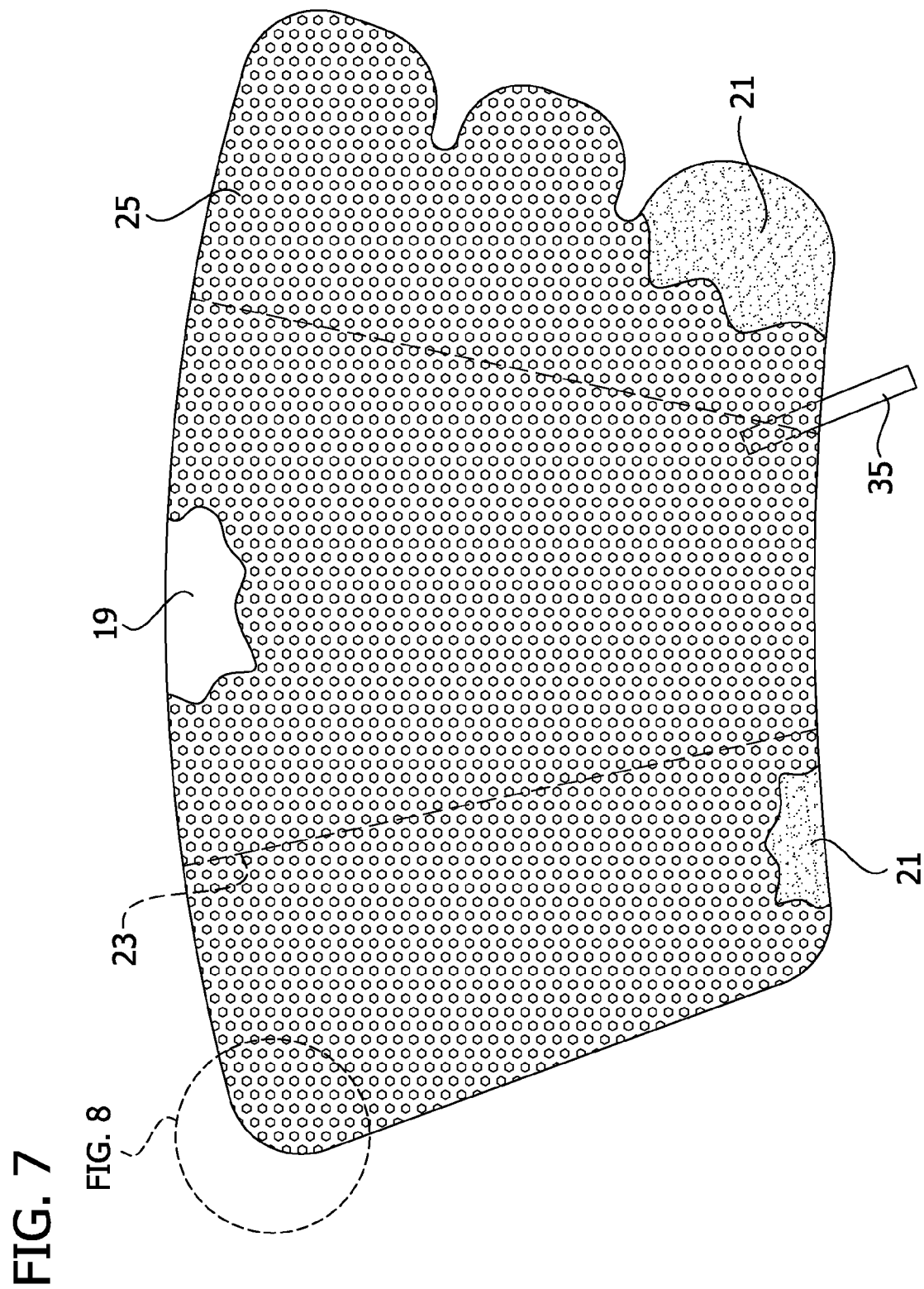
FIG. 7 is a front view of the sleeve of FIG. 1 having portions of an outer cover of the sleeve broken away.
Figure 8:
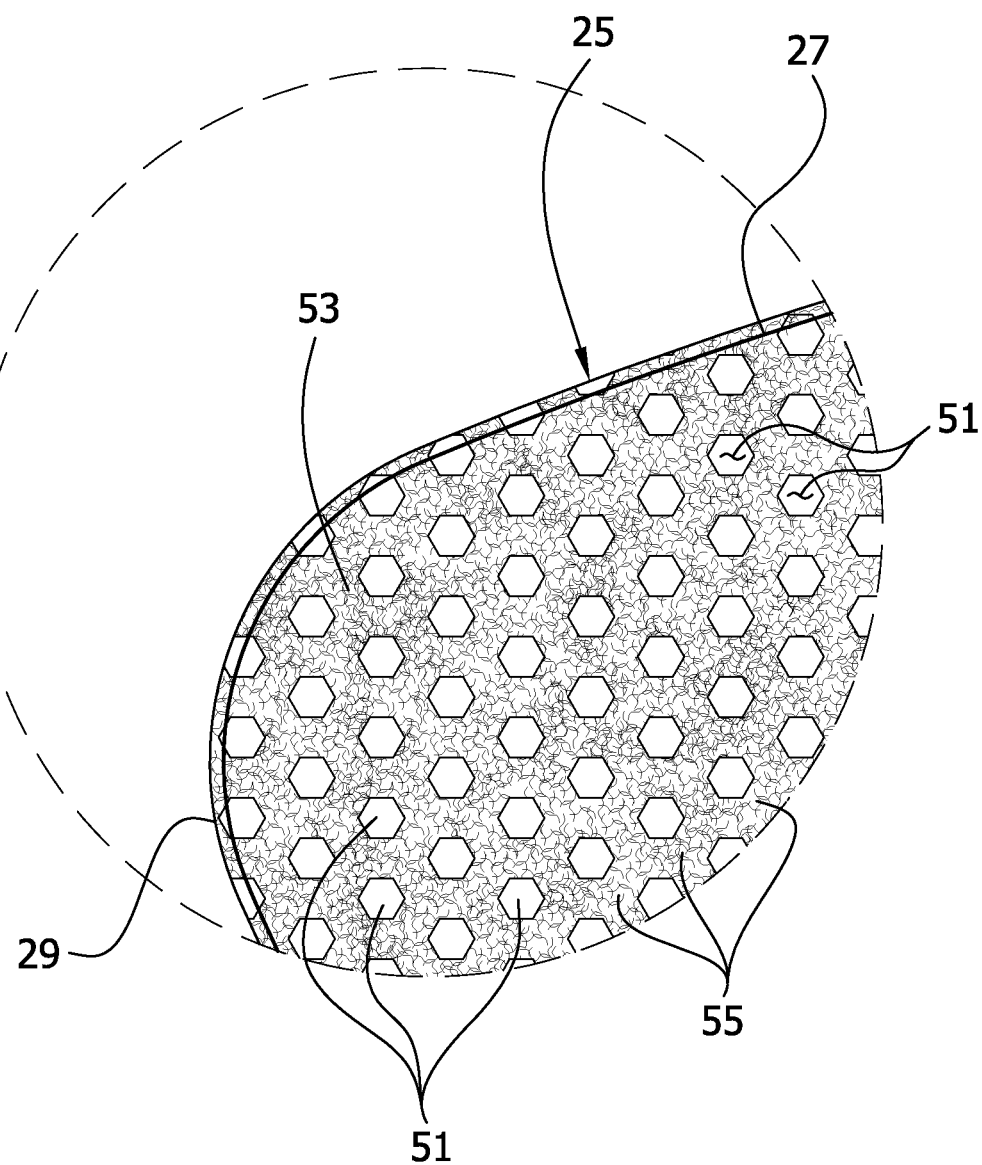
FIG. 8 is an enlarged fragmentary elevation of the outer cover of the sleeve of FIG. 1 with loop material shown.

Referring to FIGS. 4, 7 and 8, the outer cover 25 of the compression sleeve 11 may be constructed of a single sheet of material. The outer cover 25 is breathable and has a multiplicity of openings 51 or perforations so that it has a mesh construction to enhance breathability, as compared to a material without openings. A suitable material for the outer cover 25 may be a polyester mesh. The rate of evaporation from the openings is improved by treating the fibers of the mesh material with a hydrophilic material such that the outer cover includes hydrophilic fibers 53. Such treated mesh material will absorb the wicked fluid more readily, as compared to untreated mesh material. Hydrophilic fibers 53 lower the surface tension of the mesh material of the outer cover 25 to allow bodily fluids to more easily move through the cover 25 and spread therethrough for more efficient evaporation of the wicked fluid. The outer cover 25 may be secured to the intermediate layers 21 along the seam line 27, which runs adjacent only to the outer periphery 29 of the sleeve 11. In some embodiments, the sleeve 11 can be constructed without the outer cover 25.

Referring to FIGS. 1, 2, 7, and 8, the entirety of an outer surface of the outer cover 25 can also act as a component of a fastening system for securing the sleeve 11 to the limb of the wearer. For example, the outer cover 25 can have an outer surface including loops 55 that act as a loop component of a hook-and-loop fastening system. The mesh construction has interconnected or weaved fibers 53 of material forming the outer cover 25. The loops 55 may be formed as part of the material of the outer cover 25 or otherwise disposed on the surface of the outer cover. A suitable material with such construction is 100% polyester knit brushed mesh fabric with hydrophilic treatment. Hook components 57 are attached to an inner surface of an inner layer 13 at proximal, intermediate and distal flaps 59a, 59b, 59c, respectively. The loops 55 of the outer cover 25 allow the hook components 57 to be secured anywhere along the outer surface of the outer cover when the sleeve 11 is wrapped circumferentially around the limb of the wearer. This allows for sleeve 11 to be of a substantially one-size-fits-all configuration with respect to the circumferences of different wearers' limbs. Moreover, as compared to an outer cover without loops, the outer cover 25 having the loops 55 facilitates quick and robust securement of the sleeve 11 to the wearer's limb without needing to align the fastening components.

The outer cover 25 may be capable of wicking fluid in addition to being breathable. For example, the outer cover 25 may be constructed of the same material as the inner layers 13 (e.g., CoolDry model number CD9604, described above). In this way, the moisture wicked by the inner layers 13 may be wicked by the outer cover 25 through the seam line 27. The moisture will then spread out evenly across the outer cover 25 and will be able to evaporate more readily than if the outer cover was not formed of a wicking material. Wicking the fluid through the outer cover 25 will allow the fluid to move to the open areas more quickly for evaporation. The capillary effect is made more efficient as the fluid at the openings 51 is moved more quickly through the outer cover 25. Alternatively, the cover 25 can have a wicking material (not shown) laced in or on top of cover. The intermediate layers 21 may also have openings (not shown) to place a greater surface area of the inner layers 13 in registration with the outer cover 25.

Figure 9:
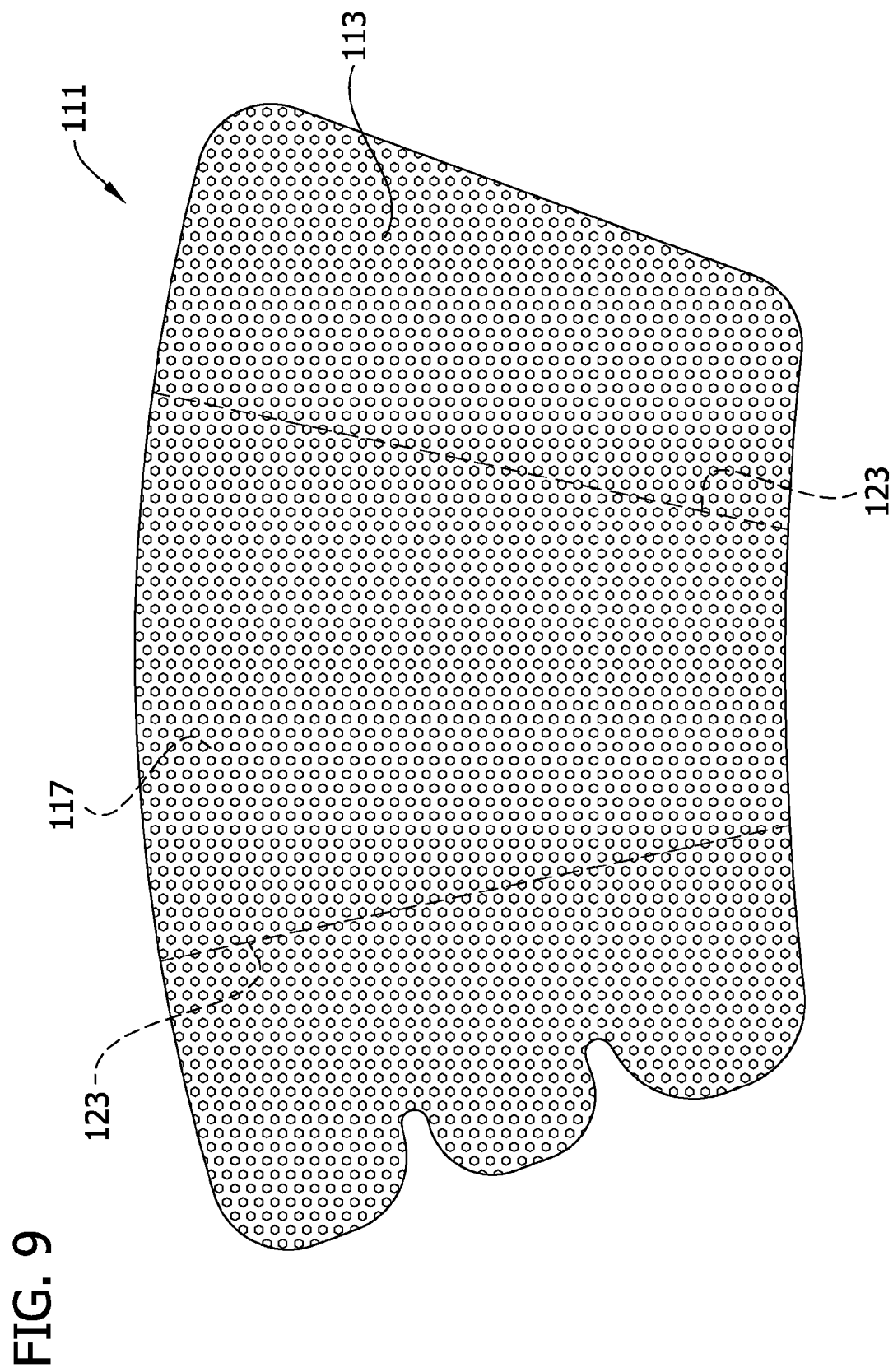
FIG. 9 is a rear view of a compression sleeve.
Figure 10:
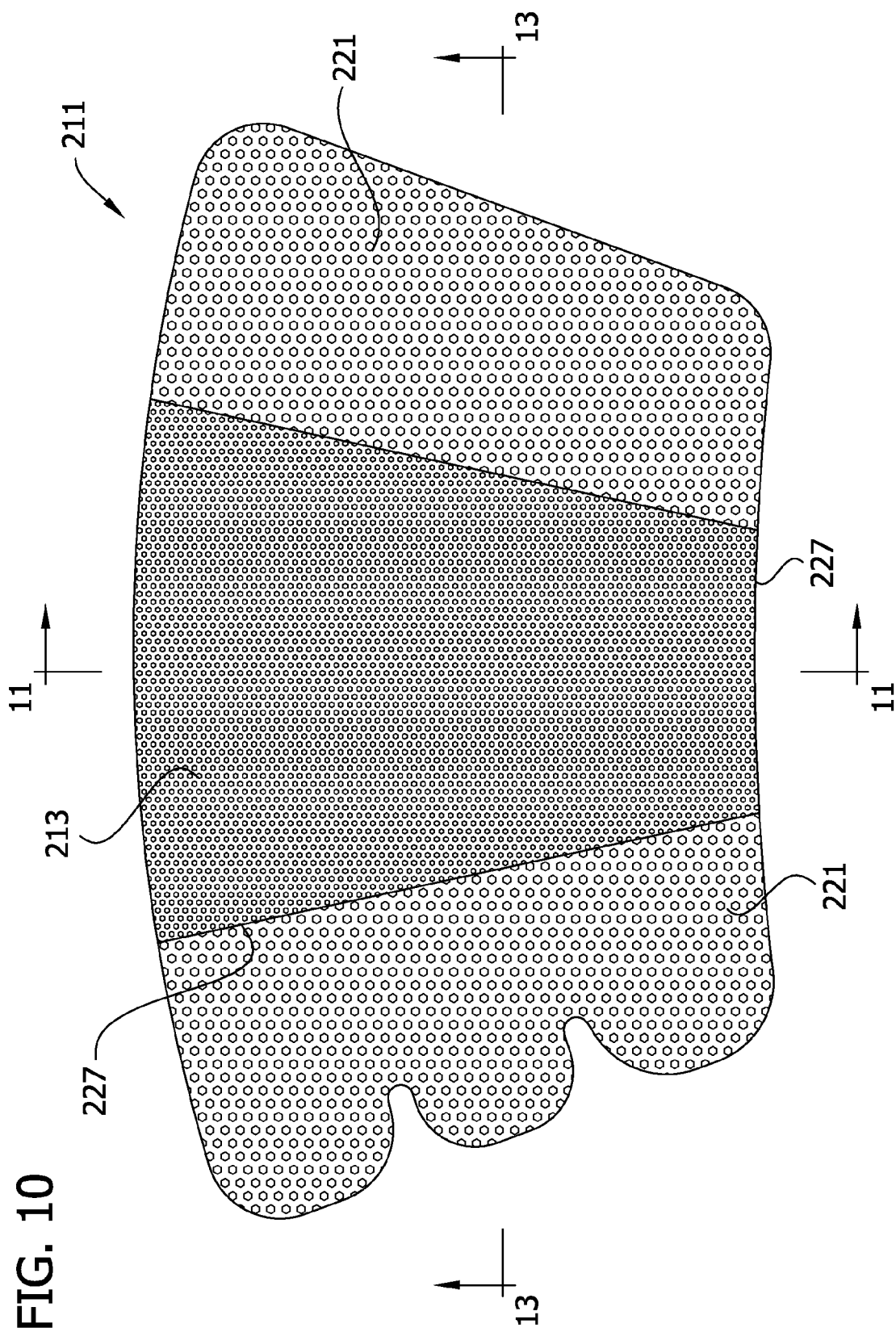
FIG. 10 is a rear view of a compression sleeve.
Figure 11:
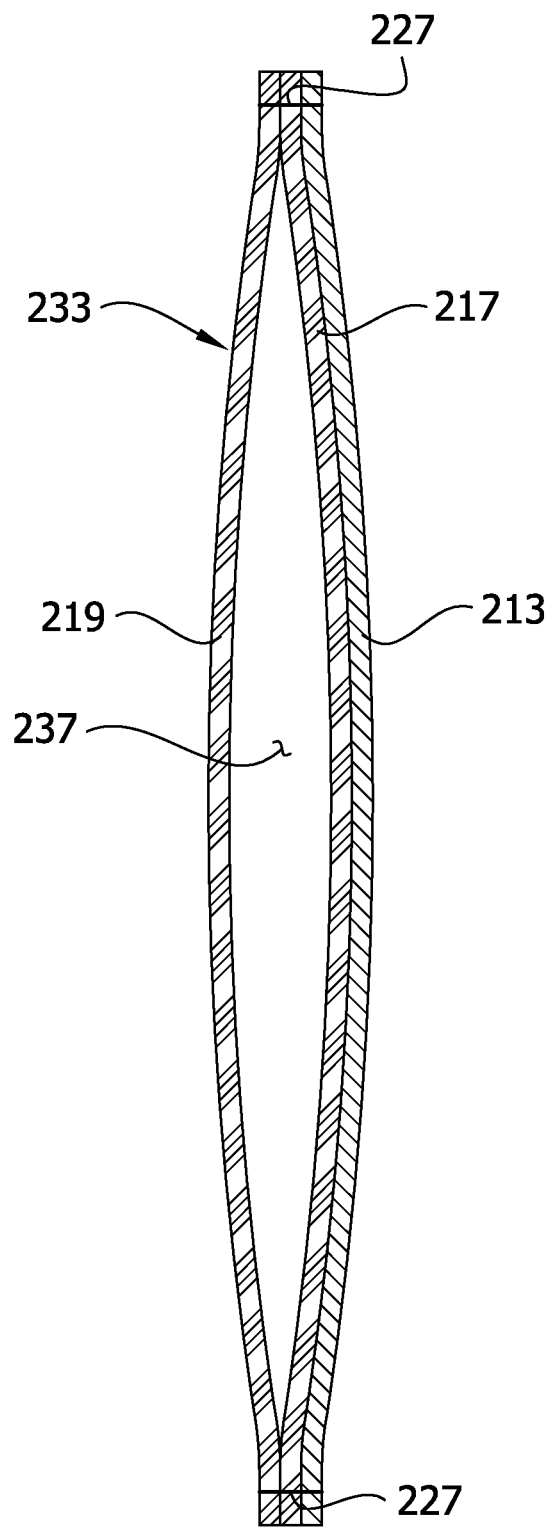
FIG. 11 is a section taken through line 11-11 of FIG. 10.
Figure 12:
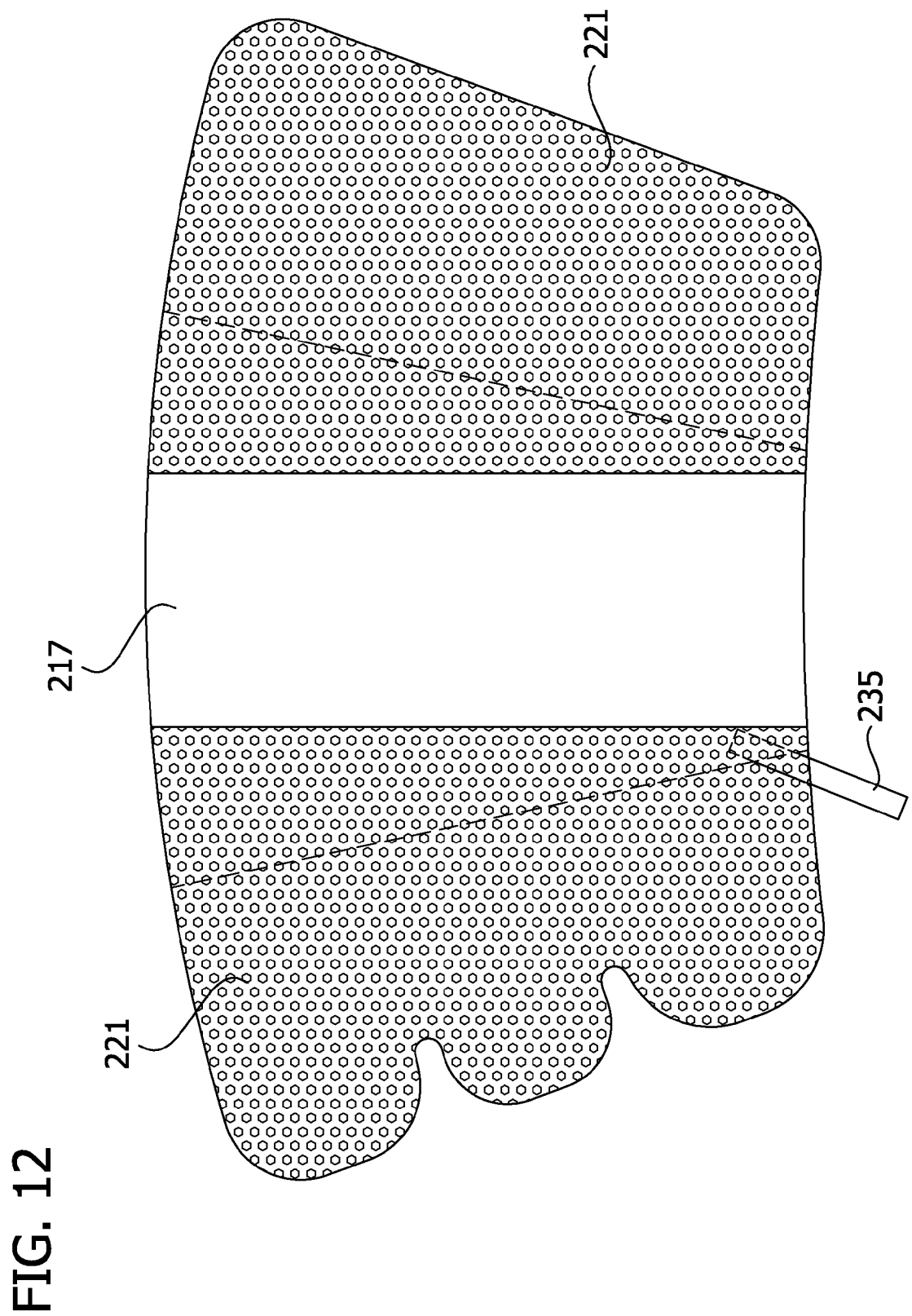
FIG. 12 is a rear view of the compression sleeve shown in FIG. 10 with an absorbent layer of the sleeve removed.
Figure 13:
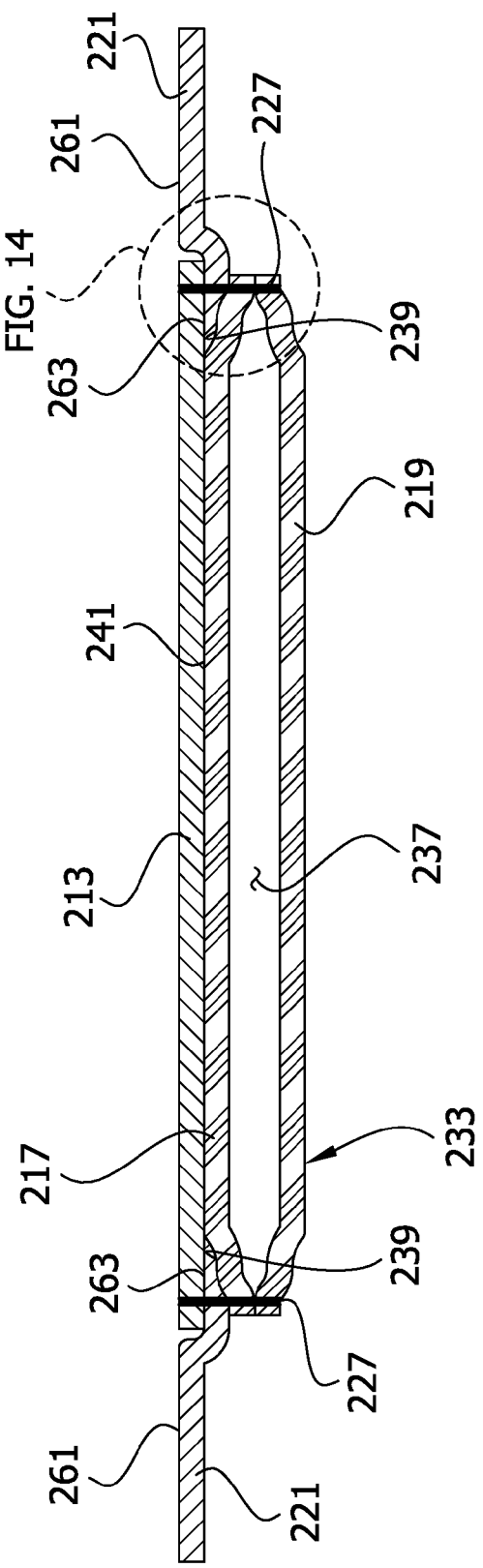
FIG. 13 is a section taken through line 13-13 of FIG. 10.

While sleeves have been described as having inner layers disposed on either side of a center portion of a bladder, the configurations are additionally or alternatively possible. For example, referring to FIG. 9, a compression sleeve 111 includes an inner layer 113. The inner layer 113 includes a single layer that extends across the entire width of the sleeve. An outline of a first bladder layer 117 and its opposing side edges 123 are also shown. The sleeve 111 functions substantially the same as the sleeve 11 (FIGS. 1-8).

Referring to FIGS. 10-14, a compression sleeve 211 includes an inner absorbent layer 213, on which a pair of intermediate garment layers 221 is overlaid. A first bladder layer 217 overlies the inner layer 213 and intermediate layers 221. And a second bladder layer 219 overlies the first bladder layer 217, forming a bladder 233. The pair of intermediate garment layers 221 are disposed on the first bladder layer 217 such that the garment layers cover side portions 239 of the bladder 233 but do not cover a center portion 241 of the bladder. The garment layers 221 extend transversely away from the bladder layers 217, 219 and inner layer 213. The garment layers 221 may also extend around the bladder 233 and cover an outer surface of the second bladder layer 219 (not shown). Additionally or alternatively, an outer layer or cover (not shown) may overlie and be secured to the second bladder layer 219 and/or intermediate garment layers 221 depending on the construction of the garment layers as described above. The layers of the sleeve 211 may be secured together by radiofrequency welding, adhesive, or other chemical and/or mechanical process. For example, the layers can be secured by a weld 227 extending around a periphery of the inner layer 13 and bladder layers 217, 219.

In use, the inner layers 213 and garment layers 221 contact the wearer's skin when the sleeve is worn.

The first and second bladder layers 217, 219 may be sealingly secured to each other along the seam line 227 forming the bladder 233. The bladder 233 defines an interior space 237 that expands and contracts under the influence of air pressure or other fluids delivered through a conduit 235 in fluid communication with the interior space 237 of the bladder 233. The interior space 237 defines a compression region of the bladder 233, the compression region being generally bounded by the seam lines 227 to provide an air or water tight boundary for the compression region. The bladder layers 217, 219 may be secured together at locations other than the seam line 227, for example, to form multiple bladders. The seam 227 also attaches the intermediate garment layers 221 to the bladder layers 217, 219.

The inner layer 213 can be formed from an absorbent material such as polyethylene SMS (spunbound-meltblown-spunbound) material and can have a soft texture to provide a comfortable interface with the wearer's body. The inner absorbent layer 213 can hold fluid, such as perspiration, at the patient's skin (i.e., perspiration) for eventual removal from the patient's skin as will be explained below. As used in the present disclosure, "absorbent" refers to a characteristic of a material whereby the material takes in moisture with little to no transfer of the moisture within the material. Thus, the absorbent material of the inner layer 213 will eventually become saturated if kept in constant contact with fluid, as compared to a wicking material which transports fluid within the material.

The garment layers 221 can be constructed of a material capable of wicking moisture near a patient's skin. The garment (or "wicking") layers 221, through capillary action along a yarn filament surface of the layers, draw in moisture trapped near the skin of the wearer, and carry the moisture away from the surface of the skin, transporting the moisture from locations on the limb at the inner layer 213 where the moisture is abundant to areas where it is less abundant for evaporation to the ambient environment. This moisture transport can be done both through the portion 261 configured for contacting the wearer's skin, and through the portion 263 which overlies and contacts the inner absorbent layer 213. The portion 263 contacting the absorbent layer 213 can draw fluid held by the absorbent layer out of the absorbent layer and into the wicking layer 221 for evaporation to atmosphere at portion 261. Fluid is also wicked through the seam 227 by wicking fibers 243 (FIG. 14) of the wicking layers 221 extending through the weld to the inner surface of the absorbent layer 213 for contacting the wearer's skin and through the bladder layers 217, 219 for transporting fluid from the wearer's skin to atmosphere at the weld.

Figure 14:
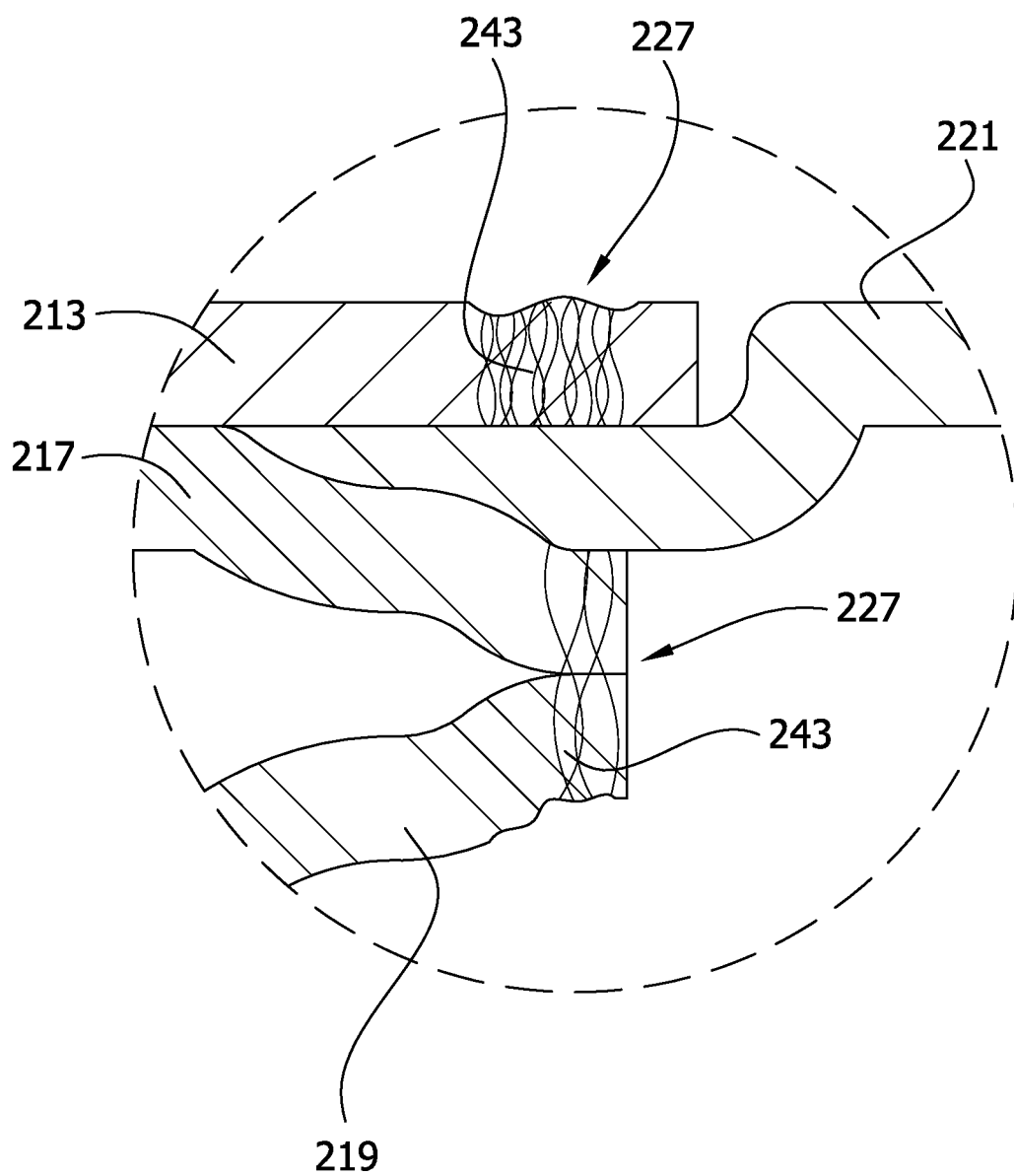
FIG. 14 is an enlarged detail of a seam line shown in FIG. 13.
Figure 14A:
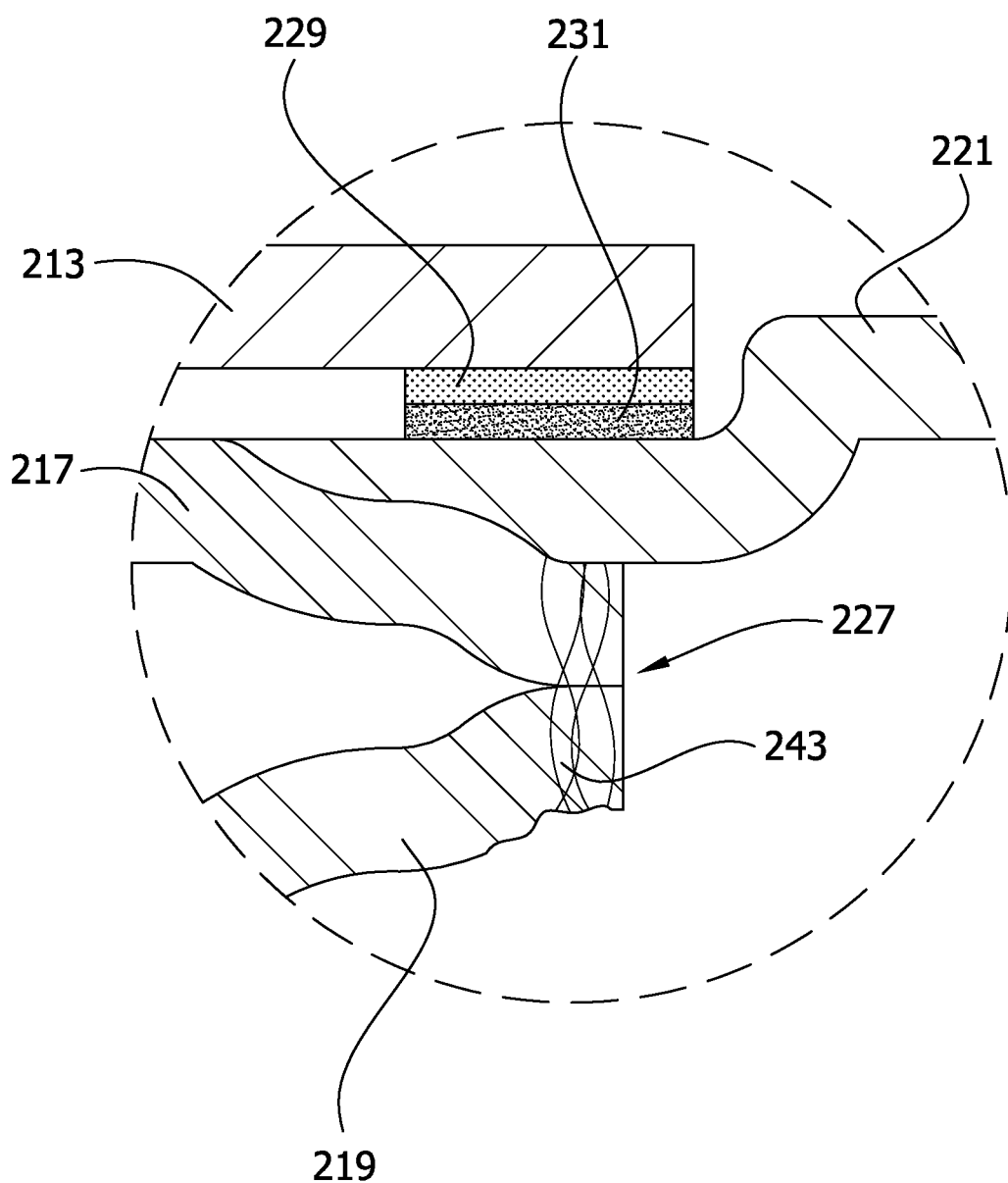
FIG. 14A is an enlarged section of the compression sleeve in FIG. 13 with the absorbent layer releasably attached to the sleeve.

In some embodiments, the inner layer 213 can be removably attached to the garment layers 221 and first bladder layer 217. In such embodiments, the inner layer 213 can be attached to the garment layers 221 by hook and loop fasteners 229, 231 (FIG. 14A) or adhesive (not shown). Additionally or alternatively, the inner layer 213 may be disposable. In certain embodiments, the garment layers 221 are fixedly attached to the bladder 233.

Figure 16:
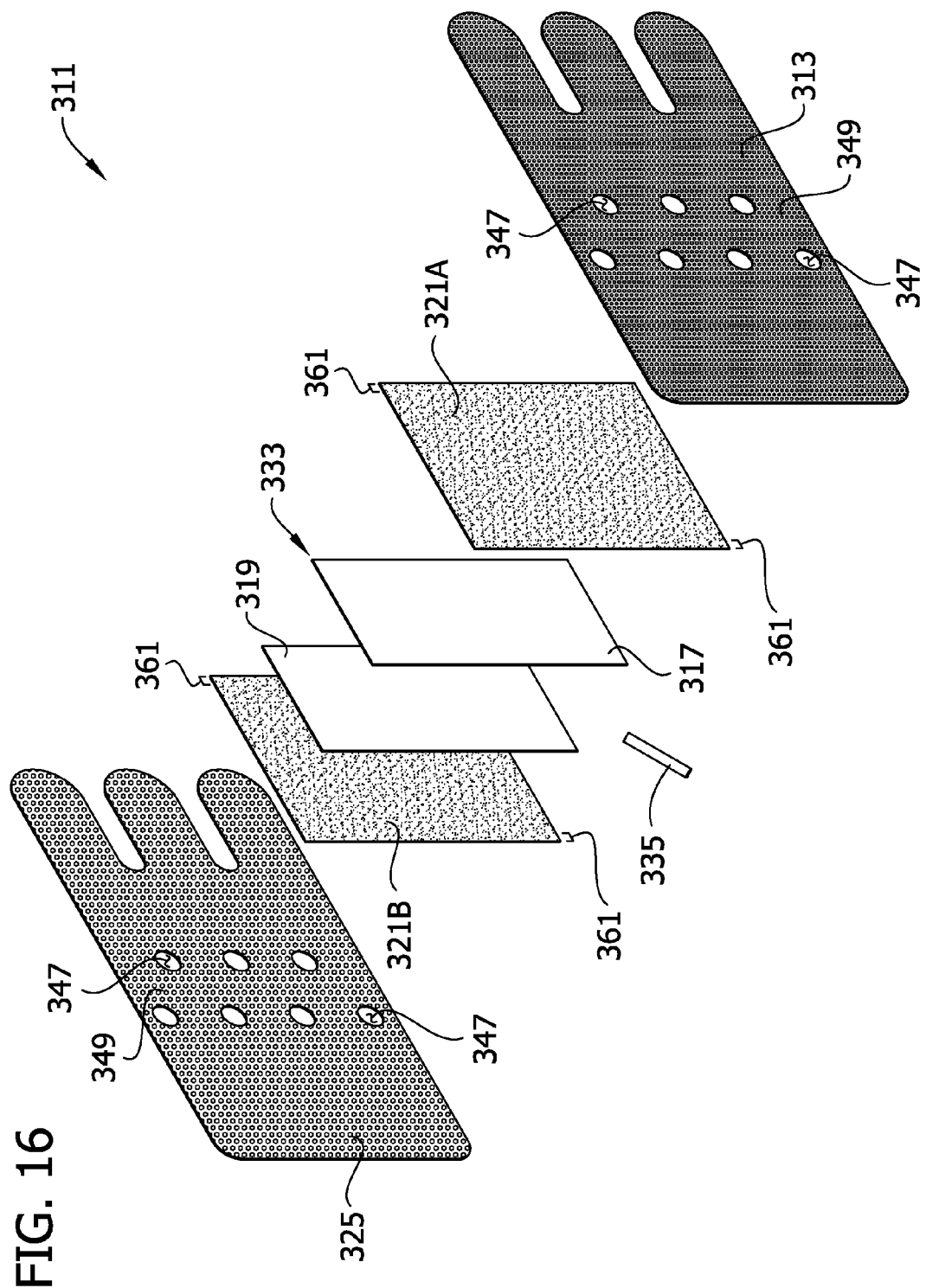
FIG. 16 is an exploded view of the compression sleeve in FIG. 15.
Figure 17:
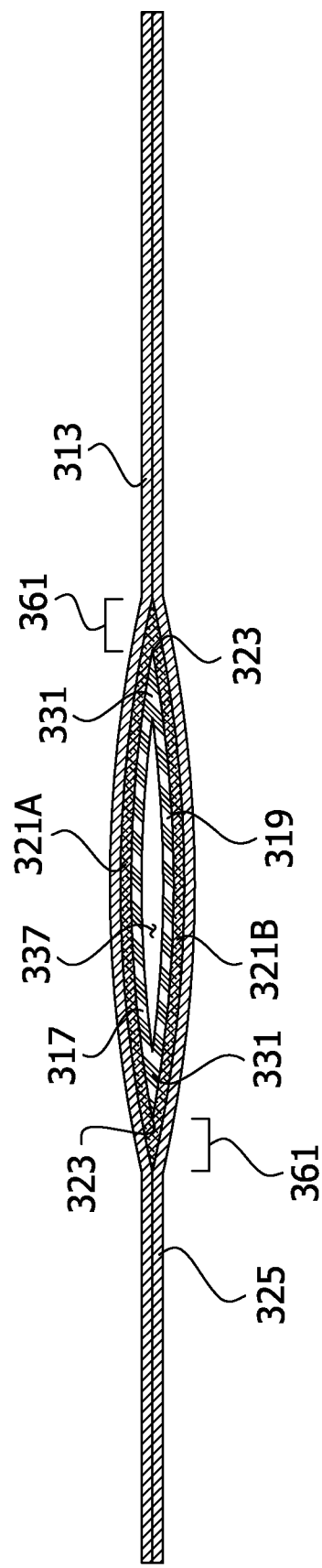
FIG. 17 is a section taken through line 17-17 of FIG. 15.

Referring to FIGS. 15-17, a compression sleeve 311 includes six layers secured together. The compression sleeve 311 includes an inner layer 313, on which a first intermediate garment layer 321A is overlaid. A first bladder layer 317 is adjacent the first garment layer 321A. And a second bladder layer 319 is adjacent the first bladder layer 317 and is secured thereto. A second intermediate garment layer 321B is adjacent the second bladder layer 319. An outer layer 325 overlies and is secured to the second garment layer 321B. The layers may be secured together by radiofrequency welding, adhesive, or other chemical and/or mechanical process. The layers are secured about a periphery 327 of the sleeve 311. In use, the inner layer 313 may be disposed most adjacent to the skin of the wearer and may be in contact with the skin of the wearer, and the outer cover 325 may be most distant from the skin of the wearer. It is to be understood that the other configurations of the layers are also possible. For example, more or fewer layers may be used.

The first and second bladder layers 317, 319 may be sealingly secured to each other along a seam line 331 extending alongside edges 323 of the bladder layers. The bladder layers 317, 319 can be made of pliable PVC. The seam line 327 attaching the layers of the sleeve 311 together also seals the bladder layers 317, 319 to each other at top and bottom edges 324, 326 of the bladder layers. The seam lines 327 and 331 along the bladder layers 317, 319 form the bladder 333. The bladder is attached only to the other layers of the sleeve 311 at the top and bottom edges 324, 326 of the bladder layers. The side edges 323 are free of direct connection to the other layers of the sleeve 311. The bladder 333 defines an interior space 337 that expands and contracts under the influence of air pressure or other fluids delivered through a conduit 335 in fluid communication with the interior space 337 of the bladder 333. The interior space 337 defines a compression region of the bladder 333, the compression region being generally bounded by the seam lines 327, 311 to provide an air or water tight boundary for the compression region. The bladder layers 317, 319 may be secured together at other locations to form multiple bladders without departing from the scope of the present invention. It is also envisioned that the bladder layers 317, 319 can be welded together to form the bladder 333 and the bladder can be stitched to the remaining layers at the top and bottom edges 324, 326 of the bladder to secure the bladder to the remaining layers.

The inner layer 313 and/or outer cover 325 can be made of a polyester material and can have openings 347 extending completely through center portions 349 of the layers. The garment layers 321A, 321B can be made from wicking material. The garment layers 321A, 321B can also extend laterally beyond the side edges 323 of the bladder layers 317, 319 so that side portions 361 of the garment layers 321A, 321B directly oppose each other instead of opposing the bladder 333. The side portions 361 can also be welded to each other along a seamline (not shown). The garment layers 321A, 321B may also extend to the top and bottom edges 324, 326 of the bladder 333 and be attached via the weld 327 or stitching as previously described. In such embodiments, when the sleeve 311 is worn, fluid (e.g., perspiration) at the inner layer 313 can be drawn out of the inner layer by the first garment layer 321A and wicked through the first garment layer to the top, bottom, and side portions 361 of the first garment layers for transferring the fluid around the bladder 333 to the second garment layer 321B. Fluid at the side portions 361 is transferred from the first garment layer 321A to the second garment layer 321B around the side of the bladder 333. Fluid at the top and bottom of the bladder 333 will wick through the seam line 327 and be transferred from the first garment layer 321A to the second garment layer 321B through a wicking process similar, for example, to the wicking process described with respect FIGS. 1-8. In embodiments in which the bladder 333 is stitched to the remaining layers, fluid at the top and bottom of the bladder can transfer from the first garment layer 321A to the second garment layer 321B through holes in the bladder material formed by the stitching.

Also, the openings 347 in the inner layer 313 allow the first garment layer 321A to directly contact the wearer's skin for wicking fluid directly from the wearer's skin. The fluid from the wearer's skin is also wicked to the top, bottom, and side portions 361 of the first garment layer 321A and around the bladder 333 to the second garment layer 321B for evaporation to the atmosphere. The openings 347 in the outer cover 325 increase the rate of fluid evaporation to the atmosphere by exposing the outer surface of the second garment layer 321B to ambient or surrounding air. Each opening 347 can have an area between about 0.50 in$^2$ (3.23 cm$^2$) and about 0.90 in$^2$ (5.81 cm$^2$), and preferably about 0.61 in$^2$ (3.94 cm$^2$). In the illustrative embodiment, the second garment layer 321B extends across the openings 347 of the outer cover 325. The second garment layer 321B entirely fills the openings 347.

Figure 18:
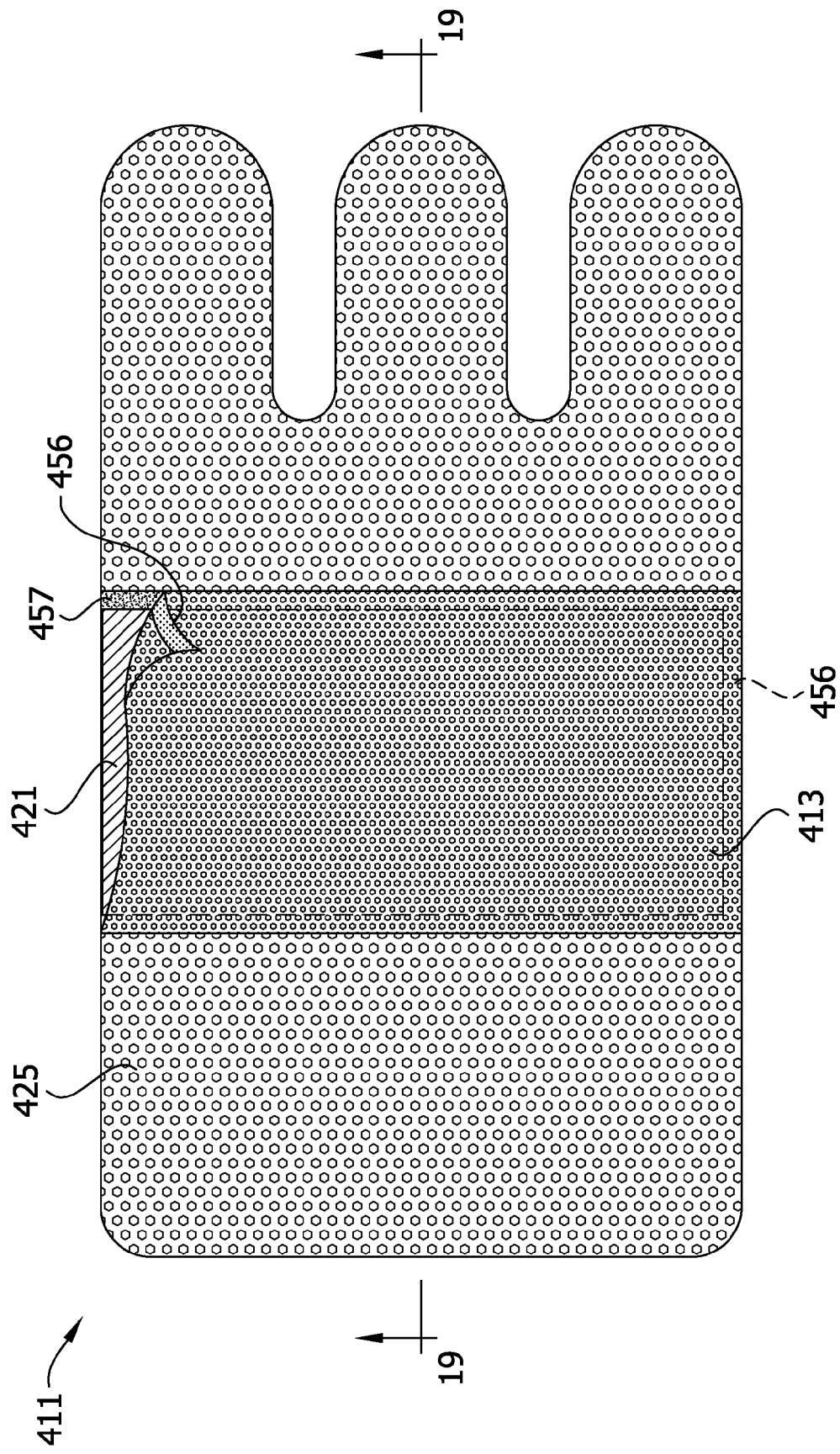
FIG. 18 a rear view of a compression sleeve.
Figure 19:
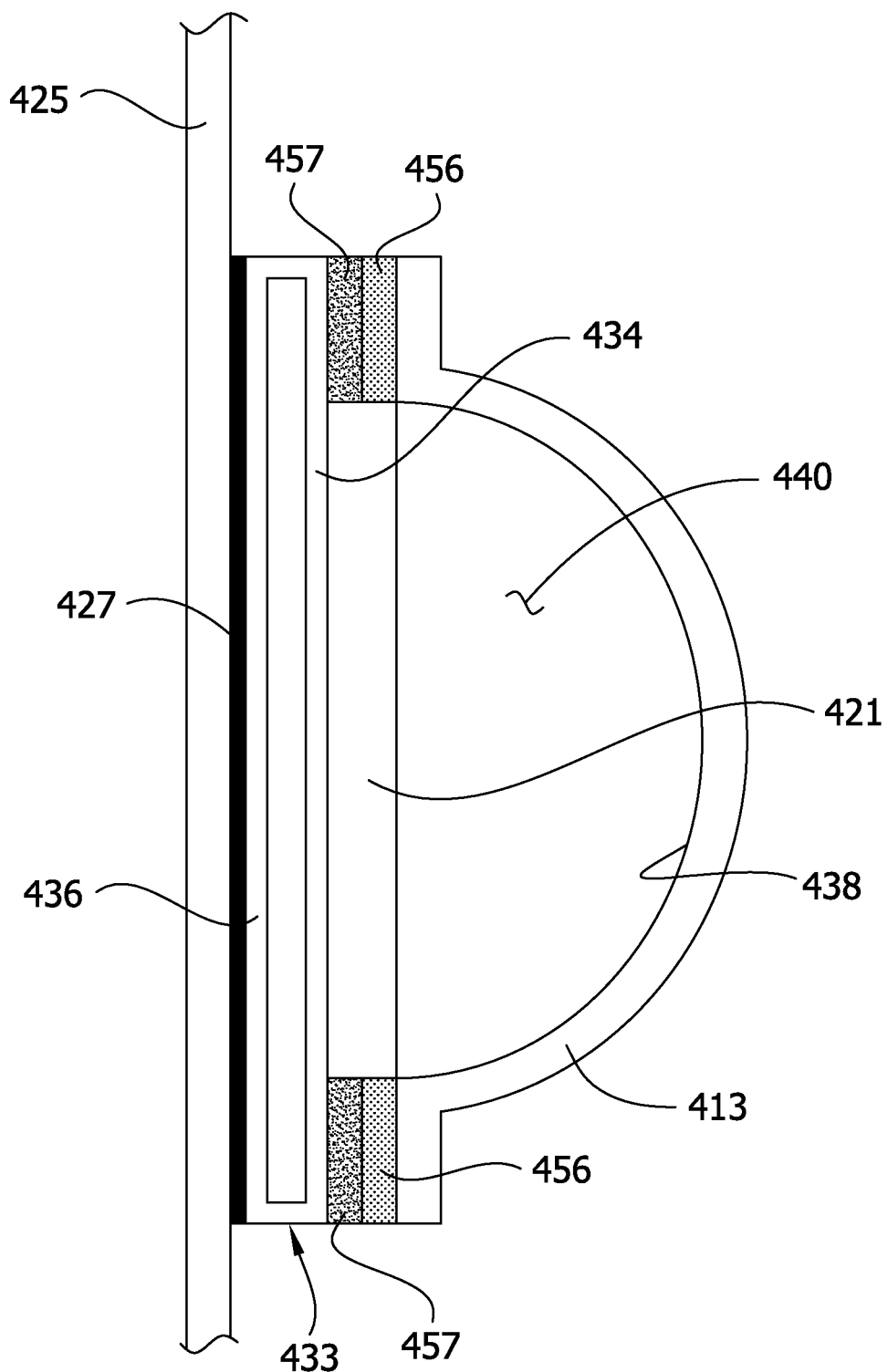
FIG. 19 is a section taken though line 19-19 in FIG. 18.

Referring to FIGS. 18 and 19, a sleeve 411 includes a bladder 433 having an inner surface 434 and an outer surface 436. The outer surface 436 of the bladder 433 is attached to an outer layer 425 by a weld 427. However, it is understood that the bladder 433 may be secured to the outer layer 425 by radiofrequency welding, adhesive, or other chemical and/or mechanical process. In some embodiments, the bladder 433 is releasably attached to the outer layer 425 such as by hook and loop fasteners (not shown). It is understood that, the outer layer 425 may be constructed similarly to the outer layers 25, 325 described above.

An inner liner 413 may be releasably attached to the bladder 433 such that the liner forms a pocket 438 defining an intermediate space 440 between the liner and the bladder. The inner liner 413 may be formed from a wicking material. The liner 413 can be attached to the bladder 433 by hook and loop strips 456, 457. Loop strips 457 are attached to the bladder 433 alongside and bottom edges of the bladder, and hook strips 456 are attached to the inner liner 413 alongside and bottom edges of the liner. The hook strips 456 on the liner 413 are engageable with the loop strips 457 on the bladder 433 to releasably secure the liner to the bladder. In some embodiments, the loop strips 457 are attached to the inner liner 413 and the hook strips 456 are attached to the bladder 433. Additionally or alternatively, the liner 413 can be releasably attached to the bladder 433 by adhesive strips (not shown). The inner liner 413 may also be releasably attached to other layers of the sleeve 411 such as the outer layer 425.

An absorbent, non-wicking material 421 may be removably received in the interior space 440 of the pocket 438 formed between the liner 413 and the bladder 433. The absorbent material 421 can be an absorbent "pad" and may be formed from of a polyethylene SMS (spunbound-meltblown-spunbound) material. When the sleeve 411 is wrapped around the wearer's limb, fluid at the inner liner 413 is wicked away from the wearer's skin by the inner liner and transported to the absorbent material 421 to be absorbed by the pad. Once the absorbent pad 421 becomes saturated with fluid, the pad can be removed from the interior space, discarded and replaced with a new pad.

Having described the invention in detail, it will be apparent that modifications and variations are possible without departing from the scope of this disclosure.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects are achieved and other advantageous results attained.

As various changes could be made in the above constructions without departing from the scope of the disclosure, it is intended that all matter contained in the above description and shown in the accompanying drawings shall be interpreted as illustrative and not in a limiting sense.

What is claimed is:

1. A compression garment comprising:
   an inflatable bladder having an inner surface, an outer surface substantially opposite the inner surface, and opposing side edges extending longitudinally along a length of the bladder, at least a portion of the bladder defining a compression region expandable to apply pressure to a portion of a wearer's body;
   a non-wicking material welded to the opposing side edges of the bladder so that the non-wicking material extends laterally away from the side edges of the bladder, the non-wicking material having an inner surface and an outer surface substantially opposite the inner surface; and
   a wicking material disposed on the inner surface of the non-wicking material for wicking fluid away from the portion of the wearer's body.

2. The compression garment set forth in claim 1 wherein the wicking material extends partially over the inner surface of the bladder.

3. The compression garment set forth in claim 2 wherein the bladder further comprises a center portion and side portions, the center portion is disposed between the side portions, the wicking material extends over the side portions, and the center portion is uncovered by the wicking material.

4. The compression garment set forth in claim 3 wherein the wicking material comprises two layers, each layer separate and spaced apart from the other layer.

5. The compression garment set forth in claim 3 wherein the wicking material extends over the entire inner surface of the non-wicking material.

6. The compression garment set forth in claim 3 wherein the wicking material extending over the side portions of the bladder is welded to the bladder within the compression region, and wherein the wicking material extending over the non-wicking material is welded around a perimeter of the non-wicking material.

7. The compression garment set forth in claim 1 wherein the wicking material extends over the entire inner surface of the bladder.

8. The compression garment set forth in claim 1 wherein the non-wicking material comprises foam.

9. The compression garment set forth in claim 1 further comprising a breathable outer cover disposed over the outer surface of the bladder.

\* \* \* \* \*